US010758347B2

(12) United States Patent
Kheradvar et al.

(10) Patent No.: US 10,758,347 B2
(45) Date of Patent: Sep. 1, 2020

(54) DELIVERY SYSTEM FOR PERCUTANEOUS DELIVERY AND IMPLANTATION OF ATRIOVENTRICULAR HEART VALVES

(71) Applicant: THE REGENTS OF THE UNIVERSITY OF CALIFORNIA, Oakland, CA (US)

(72) Inventors: Arash Kheradvar, Irvine, CA (US); Gregory S Kelley, Santee, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 376 days.

(21) Appl. No.: 15/627,360

(22) Filed: Jun. 19, 2017

(65) Prior Publication Data

US 2017/0360557 A1    Dec. 21, 2017

Related U.S. Application Data

(60) Provisional application No. 62/352,236, filed on Jun. 20, 2016.

(51) Int. Cl.
*A61F 2/24* (2006.01)
*A61B 17/00* (2006.01)
(Continued)

(52) U.S. Cl.
CPC ........ *A61F 2/243* (2013.01); *A61B 17/00234* (2013.01); *A61F 2/2436* (2013.01); *A61F 2/2439* (2013.01); *A61F 9/0026* (2013.01); *A61M 25/09* (2013.01); *A61B 2017/00292* (2013.01); *A61F 2/9517* (2020.05); *A61F 2002/9511* (2013.01)

(58) Field of Classification Search
CPC ............ A61F 2002/9511; A61F 2/2442; A61F 2002/9522; A61B 17/00234; A61B 2017/00292
See application file for complete search history.

(56) References Cited

U.S. PATENT DOCUMENTS

| | | | |
|---|---|---|---|
| 2005/0143809 A1* | 6/2005 | Salahieh | A61F 2/2418 623/2.11 |
| 2007/0088431 A1* | 4/2007 | Bourang | A61F 2/2433 623/2.11 |

(Continued)

*Primary Examiner* — Shaun L David
*Assistant Examiner* — Christina C Lauer
(74) *Attorney, Agent, or Firm* — Tope-McKay & Associates

(57) ABSTRACT

Described is a delivery system for percutaneous delivery and implantation of a heart valve. The delivery system includes a handle with a sheath extending therefrom. A splay shaft extends from the handle through the sheath. At least two arms extend from the handle through the splay shaft. The at least two arms are operable for holding a heart valve. A sheath controller is housed within the handle and is operable for selectively advancing or retracting the sheath to constrain or expose a heart valve as attached with the at least two arms. A splay shaft controller is housed within the handle for allowing the user to selectively advance or retract the splay shaft to constrain or expose the at least two arms. Finally, a valve release is attached with the handle to allow a user to selectively release a heart valve as attached with the at least two arms.

16 Claims, 31 Drawing Sheets

(51) Int. Cl.
*A61M 25/09* (2006.01)
*A61F 9/00* (2006.01)
A61F 2/95 (2013.01)

(56) References Cited

U.S. PATENT DOCUMENTS

2008/0147182 A1\* 6/2008 Righini .................. A61F 2/243
 623/2.11
2011/0172764 A1\* 7/2011 Badhwar ............... A61F 2/2403
 623/2.11

\* cited by examiner

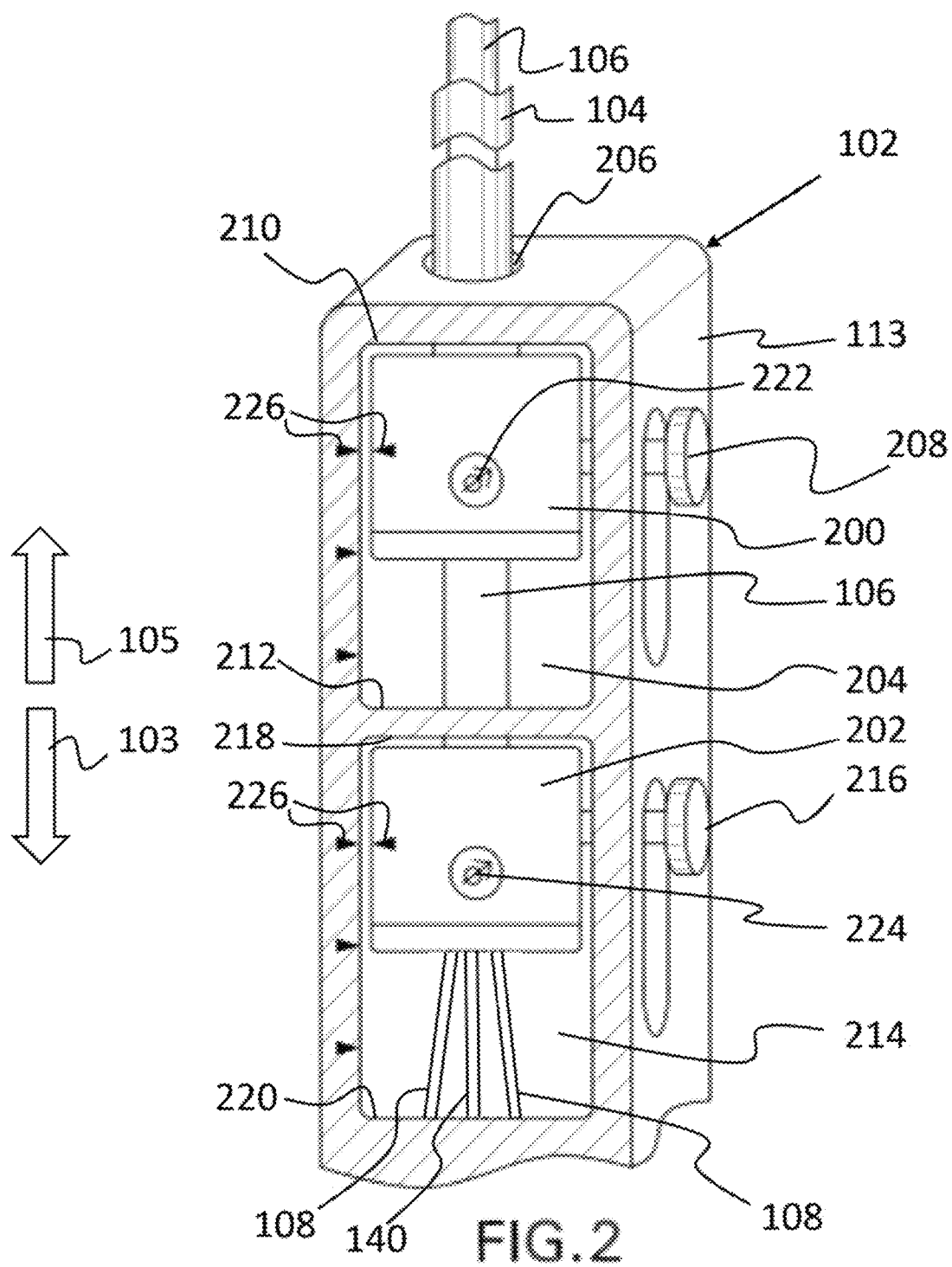

DELIVERY SYSTEM FOR PERCUTANEOUS DELIVERY AND IMPLANTATION OF ATRIOVENTRICULAR HEART VALVES

CROSS-REFERENCE TO RELATED APPLICATIONS

This is a non-provisional application of U.S. Provisional Application No. 62/352,236, filed Jun. 20, 2016, the entirety of which is incorporated herein by reference.

GOVERNMENT RIGHTS

This invention was made with government support under Grant No. HL119893, awarded by the National Institutes of Health. The government has certain rights in the invention.

BACKGROUND OF THE INVENTION

(1) Field of Invention

The present invention relates to heart valves and, more particularly, to a delivery system for percutaneous delivery and implantation of atrioventricular heart valves.

(2) Description of Related Art

Valvular heart disease is the third-most common cause of heart problems in the United States. While artificial valves have been developed to address such heart problems, such valves are often difficult to implant in a patient. Due to its minimally invasive nature, the percutaneous approach to aortic valve implantation has been a success, sparing patients aggressive surgery and reducing associated comorbidities. The lure of percutaneous technologies provides cost effective solutions to heart valve disease, thereby allowing more timely interventions with acceptable efficacy and minimal complications, especially for patients who cannot undergo surgery. Nevertheless, mitral and tricuspid valves' position present unique challenges for placing a transcatheter valve, including: inherent anatomic features of the atrioventricular valves that make fixation and perivalvular seal difficult; the lack of calcium bed (similar to aortic) in which the stented valve mechanism is securely implanted; and challenges in delivery catheter size, which must carry a relatively large prosthetic to accommodate the mitral or tricuspid valve's increased annulus diameter compared to the aortic valve.

Thus, a continuing need exists for a system for percutaneous delivery and implantation of atrioventricular heart valves.

SUMMARY OF INVENTION

The present invention relates to heart valves and, more particularly, to a delivery system for percutaneous delivery and implantation of atrioventricular heart valves. The delivery system includes a handle with a sheath extending from the handle, the sheath having a sheath lumen. A splay shaft extends from the handle through the sheath lumen. At least two arms extend from the handle through the splay shaft, the at least two arms operable for holding a heart valve. A sheath controller is housed within the handle and affixed with the sheath. The sheath controller is operable for allowing a user to selectively advance or retract the sheath to constrain or expose a heart valve when attached with the at least two arms. Additionally, a splay shaft controller is housed within the handle and affixed with the splay shaft. The splay shaft controller is operable for allowing the user to selectively advance or retract the splay shaft to constrain or expose the at least two arms.

In another aspect, a guide wire tube extends from the handle through the splay shaft. The guide wire tube provides a guide wire lumen for passage of a guide wire.

In yet another aspect, each arm comprises an arm tube with a hook wire passing therethrough.

In another aspect, the sheath controller comprises a sheath mount movably attached with the handle. The sheath mount is fixedly connected with a proximal end of the sheath. A sheath motion control is attached with the sheath mount, whereby a user can utilize the sheath motion control to move the sheath mount within the handle and thereby selectively advance or retract the sheath.

In yet another aspect, the splay shaft controller comprises a splay shaft mount movably attached with the handle. The splay shaft mount is fixedly connected with a proximal end of the splay shaft such that the splay shaft projects from the splay shaft mount and through the sheath mount into the sheath. A splay shaft motion control is attached with the splay shaft mount, whereby a user can utilize the splay shaft motion control to move the splay shaft mount within the handle and thereby selectively advance of retract the splay shaft.

In another aspect, an arm controller is attached with handle and the at least two arms. The arm controller is operable for allowing a user to selectively advance or retract at least a portion of the at least two arms.

In another aspect, the arm controller is a pivotal member and the at least two arms attached are attached with the pivotal member such that pivotal motion of the pivotal member about an axis causes at least one arm to advance while retracting at least one other arm. The at least two arms extend around the pivotal member and through the splay shaft mount and into the splay shaft.

In another aspect, a valve release is attached with the handle for allowing a user to selectively release a heart valve as attached with the at least two arms. The valve release is a valve release member movably attached with the pivotal member. The valve release member is fixedly attached with the hook wires, with the arm tubes being fixedly attached with the pivotal member, such that movement of the valve release member causes the hook wires to advance through the arm tubes which in turn causes a distal end of the hook wires to extend from a distal end of the arm tubes.

In another aspect, the distal end of the hook wire is swaged to allow the hook wire to easily bend into a hook shape to constrain a loop thereon.

Further, the at least two arms are formed such that when constrained within the splay shaft, they are relatively straight, and when the splay shaft is retracted such that a distal portion of the at least two arms extend from the splay shaft, the at least two arms splay apart from one another.

In another aspect, three arms are attached with the pivotal member such that tilting the pivotal member cause each of the three arms to selectively lengthen or shorten in direction and proportion to where each of the three arms are attached to the pivotal member.

In another aspect, the pivotal member is spherically shaped with the three arms passing around a periphery of the pivotal member.

In another aspect, a safety catch is included that is operable for selectively inhibiting motion of the valve release member, thereby preventing inadvertent release of a heart valve.

Finally, as can be appreciated by one skilled in the art, the present invention also comprises a method for forming and using the delivery system as described herein. For example, the method comprises acts of delivering a heart valve with a delivery system to a desired location inside a subject's heart chamber, such that during delivery, the heart valve is encased within a sheath; retracting the sheath to deploy the heart valve; positioning the heart valve by tilting the heart valve to align the heart valve with the subject's native annulus; and releasing and implanting the heart valve when the heart valve is aligned with the subject's native annulus. Positioning the heart valve further comprises acts of retracting a splay shaft to expose at least to arms, each of the at least two arms having a wire extending therefrom, with the wires collectively holding the heart valve; and moving a pivotal member within a handle to cause each of the at least two arms to either advance or retract and, in turn, cause the heart valve to tilt. Additionally, releasing and implanting the heart valve further comprises an act of activating a valve release member to cause each of the wires to release the heart valve. The mechanism also allows the user to selectively resheath the valve heart valve as need prior to releasing and implanting the heart valve to reposition the heart valve to a desired location. Finally, the user can selectively recapture the valve heart valve as need prior to releasing and implanting the heart valve to withdraw the heart valve if needed (such as patient complications, etc.).

BRIEF DESCRIPTION OF THE DRAWINGS

The objects, features and advantages of the present invention will be apparent from the following detailed descriptions of the various aspects of the invention in conjunction with reference to the following drawings, where:

FIG. 2 is an interior-view illustration of a distal portion of a delivery system handle according to embodiments of the present invention;

DETAILED DESCRIPTION

Figure 1A:
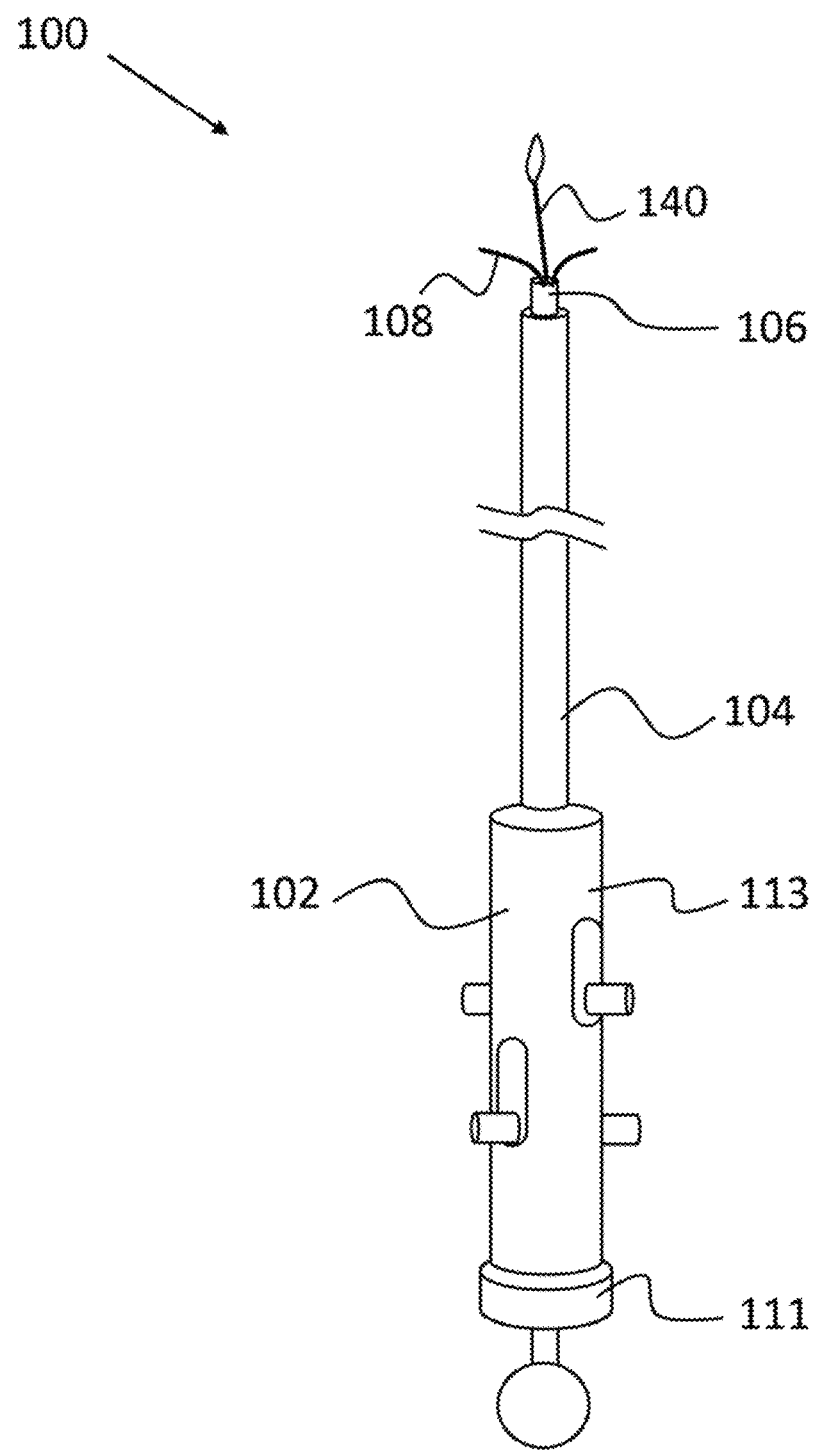
FIG. 1A is an illustration of a delivery system according to embodiments of the present invention.

The present invention relates to heart valves and, more particularly, to a delivery system for percutaneous delivery and implantation of atrioventricular heart valves. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding, of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Specific Details

This disclosure is directed to a transcatheter delivery system for atrioventricular heart valves to deliver, deploy, position, reposition and/or implant a heart valve at either mitral or tricuspid positions (or any other suitable position). In one aspect, the delivery system delivers and implants the valve through transapical approach. It another aspect, the delivery system delivers and implants the valve via an anterograde approach, such as but not limited to transfemoral, trans-subclavian, direct-aortic and trans-pulmonary pathways.

Figure 1B:
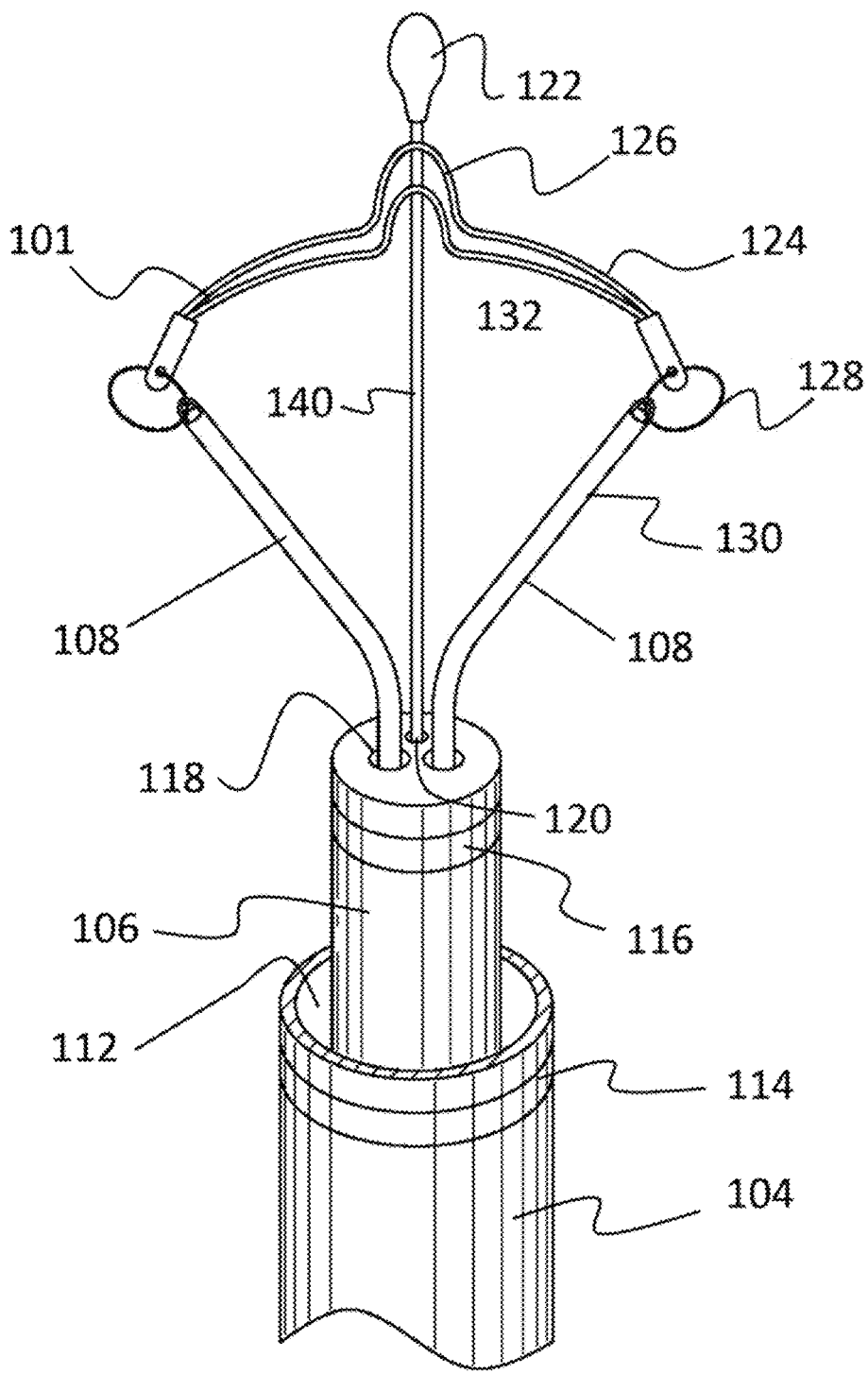
FIG. 1B is an illustration depicting a bi-leaflet valve frame as attached to a delivery catheter of the delivery system according to embodiments of the present invention.

The delivery system is illustrated in FIGS. 1A through 20 with respect to the various features as described below. Specifically and as shown in FIG. 1A, the delivery system 100 includes a handle 102 having a proximal portion 111 and a distal portion 113, with a sheath 104 extending therefrom. The sheath 104 protects and covers a splay shaft 106 which houses at least two arms 108 (three are depicted in FIG. 1A, while two are depicted in FIG. 1B) and one guide wire tube 140 that extend from the handle 102. The arms 108 and guide wire tube 140 (with guide wire therein) are used to direct, deliver, deploy and implant a heart valve. Although not depicted, it should be noted that the delivery system can also include a table mount. The table mount may be included in the handle 102 to include mounting point(s) (e.g., screw holes or screws) to secure the handle 102 in a physical position (e.g., such as a tripod or table mount). Although not required, this makes operation of the delivery system 100 more stable and easy to operate.

FIG. 1B provides a close-up view of a distal portion 113 of the delivery system, which in this non-limiting example is shown as being used to deploy a bicuspid valve 101. Specifically, FIG. 1B depicts the sheath 104 having a sheath lumen 112. The sheath 104 can be formed to include a radiopaque marker 114 for fluoroscopic visibility. Alternatively, the sheath 104 may be comprised, in whole or in part, of a radiopaque material.

The splay shaft 106 passes through the sheath lumen 112. As was the case with the sheath 104, the splay shaft 106 may also be formed to have a radiopaque marker 116 for fluoroscopic visibility. Alternatively, the splay shaft 106 may be comprised, in whole or in part, of a radiopaque material. The splay shaft 106 includes at least two arm lumens 118 and one guide-wire lumen 120. The arms 108 extend from the handle and pass through the arm lumens 118 and the guide wire tube 140 extends from the handle and passes through the guide-wire lumen 120.

The splay shaft 106 can be retracted 103 and advanced 105 with forward and back stops (as described in further detail below regarding the handle). The back stop allows the splay shaft 106 to be retracted 103 sufficiently such that the arms 108 are fully deployed (thus allowing the arms 108 to splay apart and the proximal end of the valve 101 to self-expand). The back stop is positioned such that the arms 108 can be tilted as far as necessary and will prevent the splay shaft 106 from being retracted 103 further than desired. The forward stop allows the splay shaft 106 to be advanced 105 until the arms 106 are completely within the splay shaft and prevent the splay shaft 106 from moving further. Forward and back stops can be added and/or formed at any suitable part of the delivery system. As a non-limiting example, the stops can be designed into the handle. As yet another non-limiting example, the stops can be designed into the shaft(s). A port can also be included to flush the splay shaft 106. Such a port can be incorporated into any suitable location for allowing a user to selectively flush the splay shaft 106, such as within the handle.

Referring to the arms 108, it should be noted that the term "arms" 108 as used herein refers to a construct or assembly of components that are used to releasably attach the valve. For example, the arm 108 configuration as shown in FIG. 1B includes an arm tube 130 and a hook wire 132 that is used to hold and release the Delivery System Attachment (DSA) 128 (as described in further detail below). The arm 108 is constructed of any suitable materials, non-limiting examples of which include stainless steel (SS) or desirably Nitinol wire (as the hook wire 132) and polymer tubing (as the arm tube 130).

The arms 108 also provide a means to tilt the valve 101 as described further below. The arms 108 may be formed in a desirable shape. For example, the arms 108 may be formed so that they 'splay' apart to a width which closely matches the width of the valve when it expands (when they are not constrained in the splay shaft 106). For example, the arms or wires therein (such as the hook wire, pin, etc.) can be formed such that they are bent away from one another. Further, the arms 108 may be caused to be relatively straight when they are constrained in the splay shaft 106.

Referring again to the sheath 104 and as noted above, the sheath 104 includes at least one sheath lumen 112 for allowing the splay shaft 106 to reside (e.g., slideably reside) within the sheath lumen 112. Also as was the case with the splay shaft 106, the sheath 104 can be retracted 103 and advanced 105 with forward and back stops which allow for positioning of the sheath 104 relative to the valve 101.

The heart valve 101 is drawn into and housed in the sheath 104 during delivery and positioning of the valve 101. After the valve 101 is positioned within the native valve anatomy, the sheath 104 is retracted 103, uncovering the valve 101 and allowing the distal end of the valve 101 (or implant) to self-expand. A back stop allows the sheath 104 to be retracted 103 sufficiently to uncover the valve 101 and prevent the sheath 104 from being retracted 103 further. Alternatively, a forward stop allows the sheath 104 to be advanced 105 sufficiently to cover the valve 101 and prevent the sheath 104 from being advanced 105 further.

It should be noted that the delivery system can be used to deliver any heart valve. Thus, although a bicuspid valve is depicted in FIG. 1B, the invention according to the principles of the present invention is not intended to be limited thereto. The valve 101 includes a valve frame 124 that supports a valve structure and leaflets (not shown for illustrative purposes). An example of such a valve is depicted in U.S. patent application Ser. No. 15/598,210, filed May 17, 2017, the entirety of which is incorporated herein by reference. The valve frame 124 is the mechanical structure to which the leaflets and valve structure are attached.

The heart valve 101 can include atrial catches 126 (at least two), which are features of the valve frame 124 that are intended to fit against the atrial side of the native valve when implanted to prevent the valve 101 from moving into the ventricle, while the balance of the frame 124 is intended to fit against the ventricle side of the native valve and prevent the valve 101 from moving toward the atrium. The catches 126 effectively operate to secure the valve 101 in position.

Also shown in FIG. 1B are the DSA 128 features/components (e.g. loops, or other suitable attachment feature), which are used for release-ably attaching the valve 101 to the delivery system 100. In various embodiments, the DSA 128 are loops that are attached to the valve 101 and release-ably attached to the delivery system 100. The loops can be constructed of any suitable materials, non-limiting examples of which include a suture formed of common suture materials, such as polypropylene (PP), polyethylene (PE), nylon, Ultra-high Molecular Weight Braided Polyethylene (UHMWPE), Nitinol, and stainless steel (SS). In other embodiments, the DSA 128 may be attached to the delivery system 101 and release-ably attached to the valve 101. In some embodiments, the valve 101 also includes anchors (not shown) which can be used to help secure the valve 101 in position once implanted, if needed.

As noted above, a guide wire tube 140 extends from the handle and passes through the guide-wire-tube lumen 120. Thus, in such an aspect, the guide wire tube 140 provides a lumen for passage of the guide wire not shown.

As such, incorporated in the delivery system is a guide wire tube 140 which extends from the handle 102 to a distal tip 122 (the distal tip 122 is attached or bonded to the guide wire tube 140). The guide wire is not shown in these illustrations. The guide wire is a separate device used with many medical devices and may be inserted through the guide wire tube 140 during a valve implantation procedure. A distal tip 122 of the distal end of the guide wire tube 140 generally includes a non-traumatic shape and is often tapered to facilitate maneuvering through anatomy. For example, the distal tip 122 may have a rounded outer edge. The distal tip 122 may also be comprised, in whole or in part, of a radiopaque material.

Figure 1C:
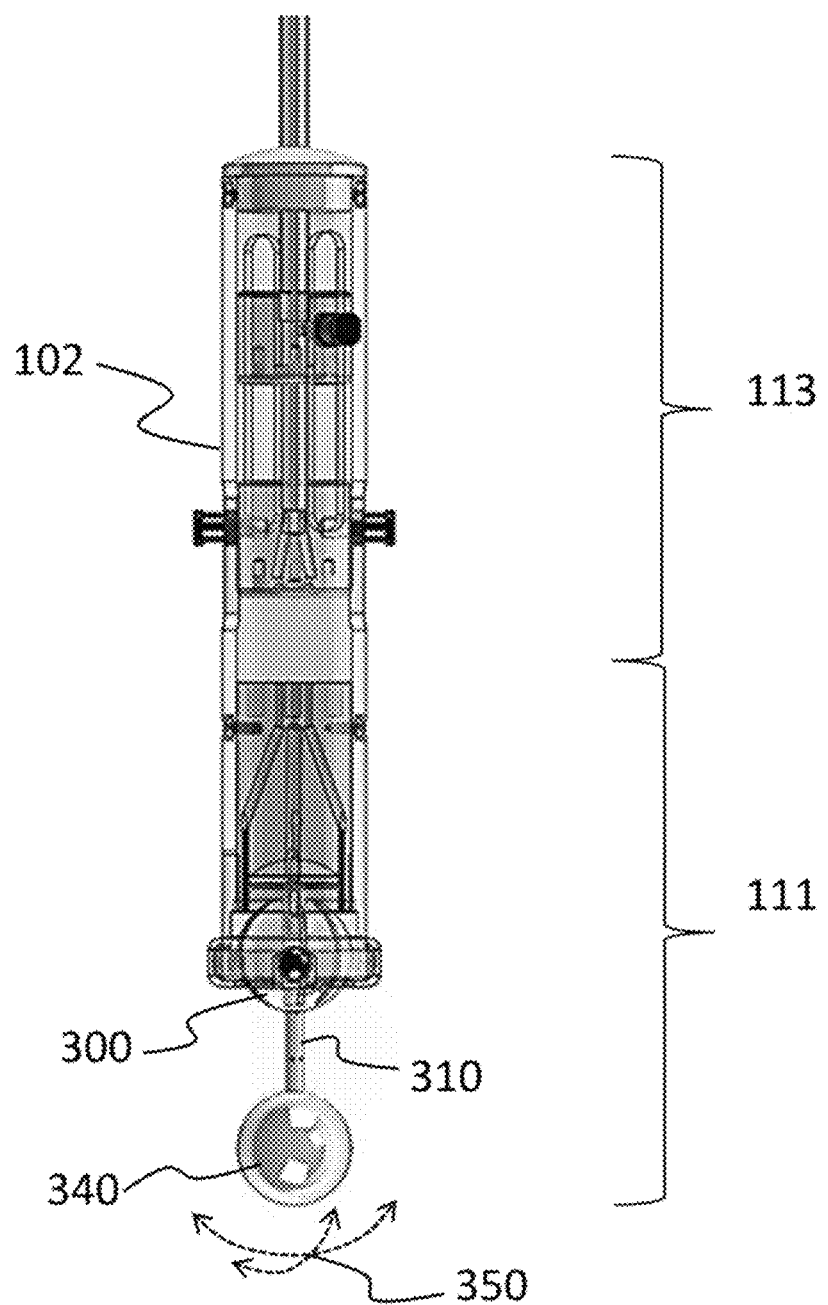
FIG. 1C is an illustration of a handle of the delivery system according to embodiments of the present invention.

As noted above, the sheath 104, splay shaft 106, and arms 108 traverse into a handle 102. As shown in FIG. 1C, the handle 102 includes a distal portion 113 and a proximal portion 111. The distal portion 113 houses a sheath controller and a splay shaft controller, while the proximal portion 111 houses the arm controller. Each of these components are described in further detail below.

For further understanding, FIG. 2 provides an interior-view of the distal portion 113 of the delivery system handle 102. As noted above, the distal portion 113 of the handle 102 houses a sheath controller and a splay shaft controller.

The sheath controller comprises a sheath mount 200 and any corresponding components that allow a user to selectively advance 105 and retract 103 the sheath 104. As a non-limiting example, the sheath mount 200 movably (e.g., slidably) resides within a cavity 204 within the handle 102 and is attached with the proximal end of the sheath 104. The sheath 104 extends from the sheath mount 200 and passes through a hole or other aperture 206 formed in the handle 102. The sheath mount 200 also includes a sheath motion control 208 that allows a user to easily retract 103 or advance 105 the sheath mount 200 within the handle 102 until reaching forward 210 or back stops 212. The sheath motion control 208 is any suitable mechanism, device, or configuration that allows a user to selectively move the sheath mount 200, non-limiting examples of which include a knob (as shown) extending from the sheath mount 200 and pins or other assemblies formed or otherwise attached with the sheath mount 200 that enable a user to easily move the sheath mount 200. Thus, because the sheath 104 is attached with the sheath mount 200, the sheath mount 200 provides a mechanism to enable retraction 103 and advancement 105 of the sheath 104.

The splay shaft 106 passes by the sheath mount 200 and into the sheath 104 such that retraction 103 and advancement 105 motion of the sheath mount 200 does not cause motion of the splay shaft 106. For example, a hole is formed through the sheath mount 200 allowing the splay shaft 106 to pass out of the sheath and through the hole and continue on until being connected with the splay shaft mount 202.

Similarly, the splay shaft controller comprises a splay shaft mount 202 and any corresponding components that allow a user to selectively advance 105 and retract 103 the splay shaft 106. As a non-limiting example, the splay shaft mount 202 movably (e.g., slidably) resides within a cavity 214 within the handle 102 and is attached with the proximal end of the splay shaft 106. The splay shaft 106 extends from the splay shaft mount 202 and passes through a hole formed in the sheath mount 200, and thereafter through the hole or aperture 206 formed in the handle 102. In various embodiments, the splay shaft 106 extends from the splay shaft mount 202 and into the sheath mourn 200, where it enters and is encompassed by the sheath 104 before leaving the handle 102. The splay shaft mount 202 also includes a splay shaft motion control 216 that allows a user to retract 103 or advance 105 the splay shaft mount 202 within the handle 102 until reaching forward 218 or back stops 220. The splay shaft motion control 216 is any suitable mechanism, device, or configuration that allows a user to selectively move the splay shaft mount 202, non-limiting examples of which include a knob (as shown) extending from the splay shaft mount 202 and pins or other assemblies formed or otherwise attached with the spay shaft amount 202 that enable a user to easily move the splay shaft mount 202. Thus, because the splay shaft 106 is attached with the splay shaft mount 202, the splay shaft mount 202 provides a mechanism to enable retraction 103 and advancement 105 of the splay shaft 106.

Position markers 226 can also be included on the handle 102 and each of the splay shaft mount 202 and sheath mount 200 to assist a user in determining the appropriate motion of each of the corresponding mounts.

Figure 4:
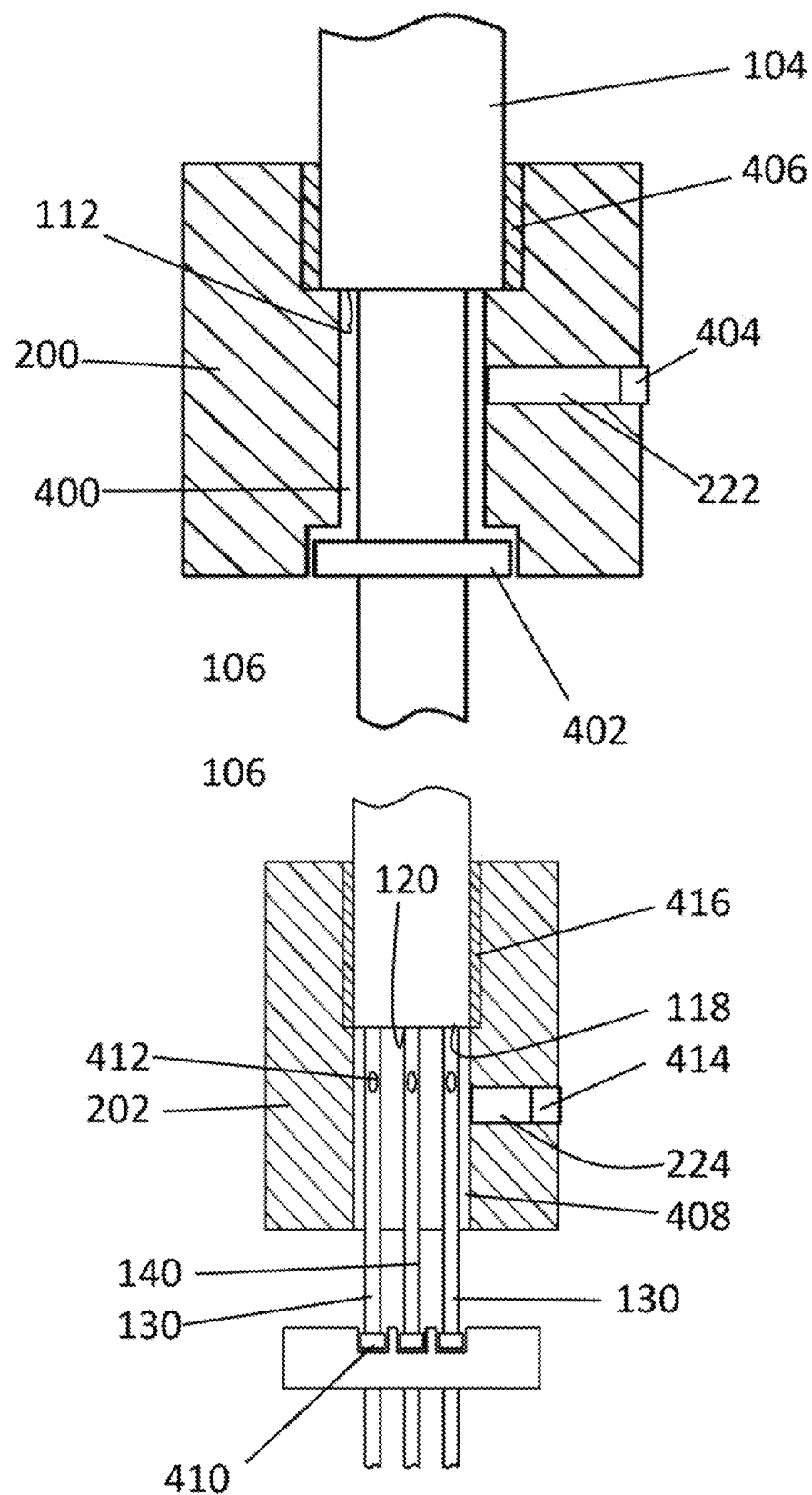
FIG. 4 is a cut-away illustration of a sheath mount and a splay shaft mount.

In various embodiments it may be desirable to flush and seal each of the sheath 104 and splay shaft 106. Thus, in various embodiments, the handle 102 is formed to include a means to facilitate flushing and sealing of the sheath 104 and/or splay shaft 106. For example, a sheath flush port 222 (with a check valve) can be included that ports into the sheath 104 and allows a user to selectively flush and seal the sheath 104. Similarly, a splay shaft port 224 (with flush valve) can also be included that ports into the splay shaft 106 and allows a user to selectively flush and seal the splay shaft 106. In various aspects, the handle 102 also includes ports or other means (e.g., holes as shown in FIG. 4) to flush the arms 108 (and arm tubes) and guide wire (and/or guide wire tube). Also as shown in FIG. 2 are the arms 108 and guide wire tube 140, which pass through the splay shaft mount 202 and into the splay shaft 106.

It should be noted that the flush operations as described in this disclosure for the various components is a desired functional need for the delivery system. The various ports or ports can be designed into the handle (or other accessible location) to allow a user to easily flush the corresponding component. For example, a saline filled syringe can be connected to the port(s) to flush the delivery system. After flushing, the system needs to be sealed to prevent blood loss during the procedure (hemostasis). Some common means to seal a lumen or port include a plug, a check valve or one way valve, and a stop-cock. Some common means to seal around a tube or shaft include o-rings or a tuohy borst valve. Thus, the seals or sealable valves described herein can use any suitable component that provides for the relative valve or sealing function.

Figure 3A:
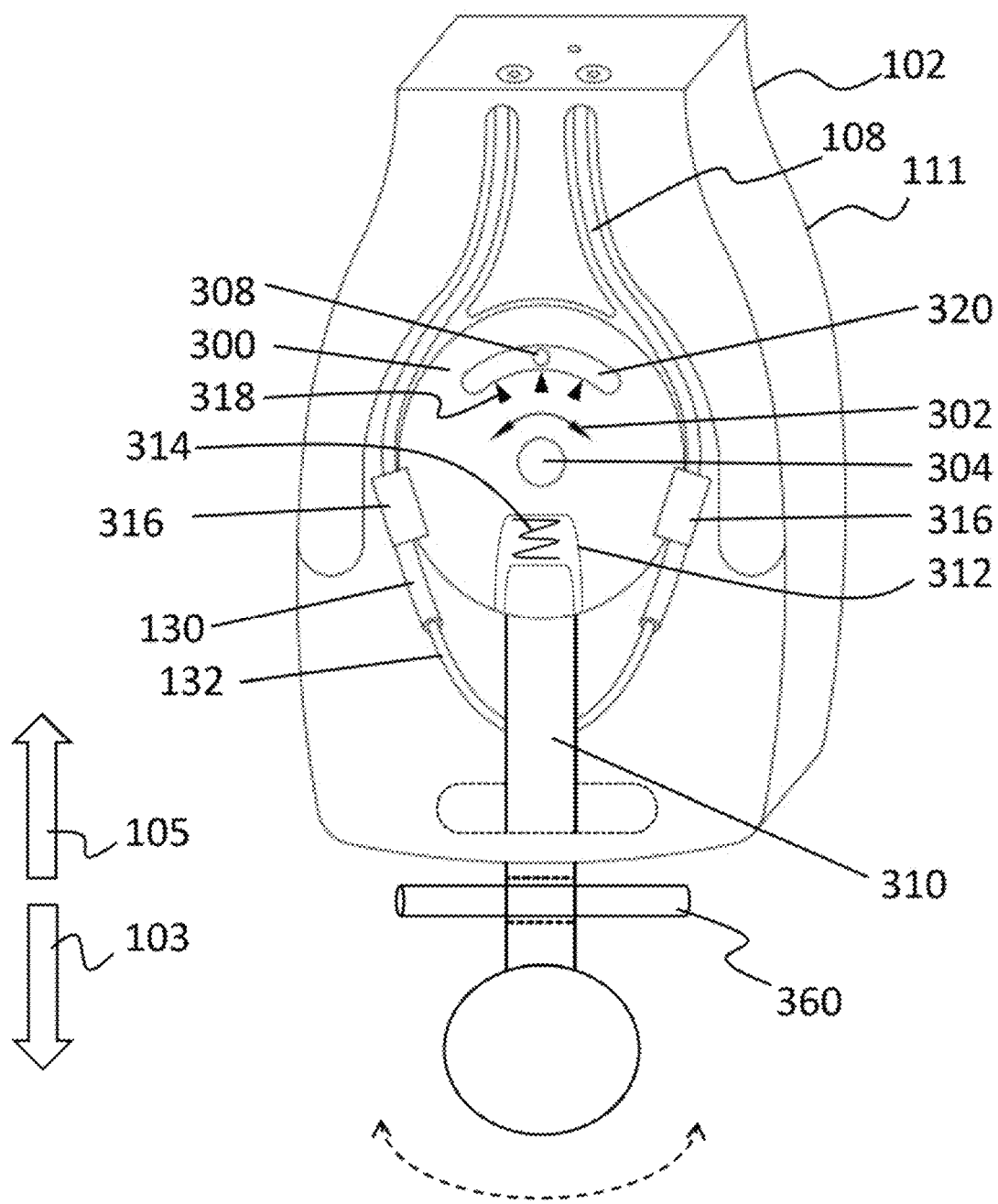
FIG. 3A is an interior-view illustration of a proximal portion of the delivery system handle according to embodiments of die present invention.

FIG. 3A is an interior-view illustration of a proximal portion 111 of the delivery system handle 102. As shown the delivery system includes an arm controller. The arm controller is any suitable mechanism or device that allows a user to selectively advance 105 and retract 103 the arms 108, or portions of the arms 108. As a non-limiting example, a pivotal member 300 is housed within the handle 102. At least two arms 108 are connected with the pivotal member 300 which may be pivoted 302 about an axis 304, to advance 105 one arm 108 while retracting 103 the other arm 108 to a desired amount, or vice versa, thereby to cause the valve to tilt in the plane of the arms 108. In various embodiments the pivotal member 300 is cylindrical shaped. The handle 102 can be formed to include stops to limit the range of motion for the action of tilting the arms 108. For example, a pin 308 can be formed to protrude from the handle 102 and pass through or otherwise reside within a slot 320 formed in the pivotal member 300. Thus, in this aspect, the rotation of the pivotal member 300 is limited by the size or shape of the slot 320.

A valve release is also included with the delivery system, which is any suitable mechanism or device for allowing a user to selectively release the valve as attached with the arms 108 and/or hook wires 132 (or other components). As a non-limiting example, the valve release comprises a valve release member 310 that is movably attached with the pivotal member 300. For example, the valve release member 310 can be a rod positioned within a slot 312 formed within the pivotal member 300. A bias member, such as a spring 314, can also be included to bias the rod or valve release member 310 away from the pivotal member 300. In the non-limiting example as shown in FIG. 3A, the valve release member 310 is shown as extending to outside the handle 102 to allow a user to pivot the pivotal member 300 (to tilt the valve) and depress the valve release member 310 to release the valve. It is should be noted that the pivotal member 300 is pivoted using any suitable mechanism, technique or device. For example, the pivotal member 300 can be exposed to allow a user to simply twist it. As another non-limiting example, the pivotal member 300 can have an attachment or other item that extends beyond the handle 102 to allow a user to pivot the pivotal member 300. In the non-limiting example as depicted in FIG. 3A, the valve release member 310 can be used to pivot the pivotal member. In various embodiments, the delivery system desirably includes a safety catch 360 that must be actuated before the valve release member 310 can be activated to release the valve. The safety catch 360 is any mechanism or device that prevents inadvertent release of the valve. In the non-limiting example as shown in FIG. 3A, the safety catch 360 is a pin that passes through a hole formed in the valve release member 310 to inhibit depressing motion of the valve release member 310. In other examples, the safety catch 360 can be a clip that clips around the valve release member 310, etc. Thus, in either example, the valve release member 310 cannot be depressed until the safety catch 360 is pulled. As can be appreciated by those skilled in the art, there are a number of ways by which a safety catch 360 can be incorporated into the delivery system to inhibit certain motions of the valve release member to prevent inadvertent release of the valve. Thus, although some examples are provided, the invention is not intended to be limited thereto.

The hook wires 132 are then each affixed with the valve release member 310, which pass from the valve release member 310 and into the arras tube 130. The arms 108 (e.g., hook wire 132 and arm tube 130) then traverse around the periphery of the pivotal member 300 (where they are clamped 316) and back toward one another and into the distal portion of the handle (as shown in FIG. 2). The shape of the pivotal member 300 in coordination with the positioning of the arms 108 allow the user to selectively advance 105 and retract 103 the arms. In other words, because the pivotal member 300 is wider in the middle than at its ends and because the arms are anchored (e.g., via the valve release member 300 and/or clamps 316), pivotal motion allows for selective motion of the arms 108. As such, the delivery system may include at least two arms 108 that are attached to a handle mechanism such that the arms 108 may be moved in opposite directions to cause an attached valve to tilt in the plane of the arm(s) 108 to facilitate alignment. In this example, the valve is connected to two arms 108 and one arm 108 is moved more distal relative to the other (2 arm system) to tilt the valve.

Position markers 318 can also be included to allow a user to view and/or otherwise asses pivotal motion of the pivotal member 300. Finally, in various embodiments, depressing or pushing in the valve release member 310 causes the hook wires 132 to advance from the arm tubes 130, which in turn releases a valve attached with the distal ends of the hook wires 132. In other aspects, the valve release member 310 can be pulled to withdraw the hook wire (or pin in examples provided below).

Figure 3B:
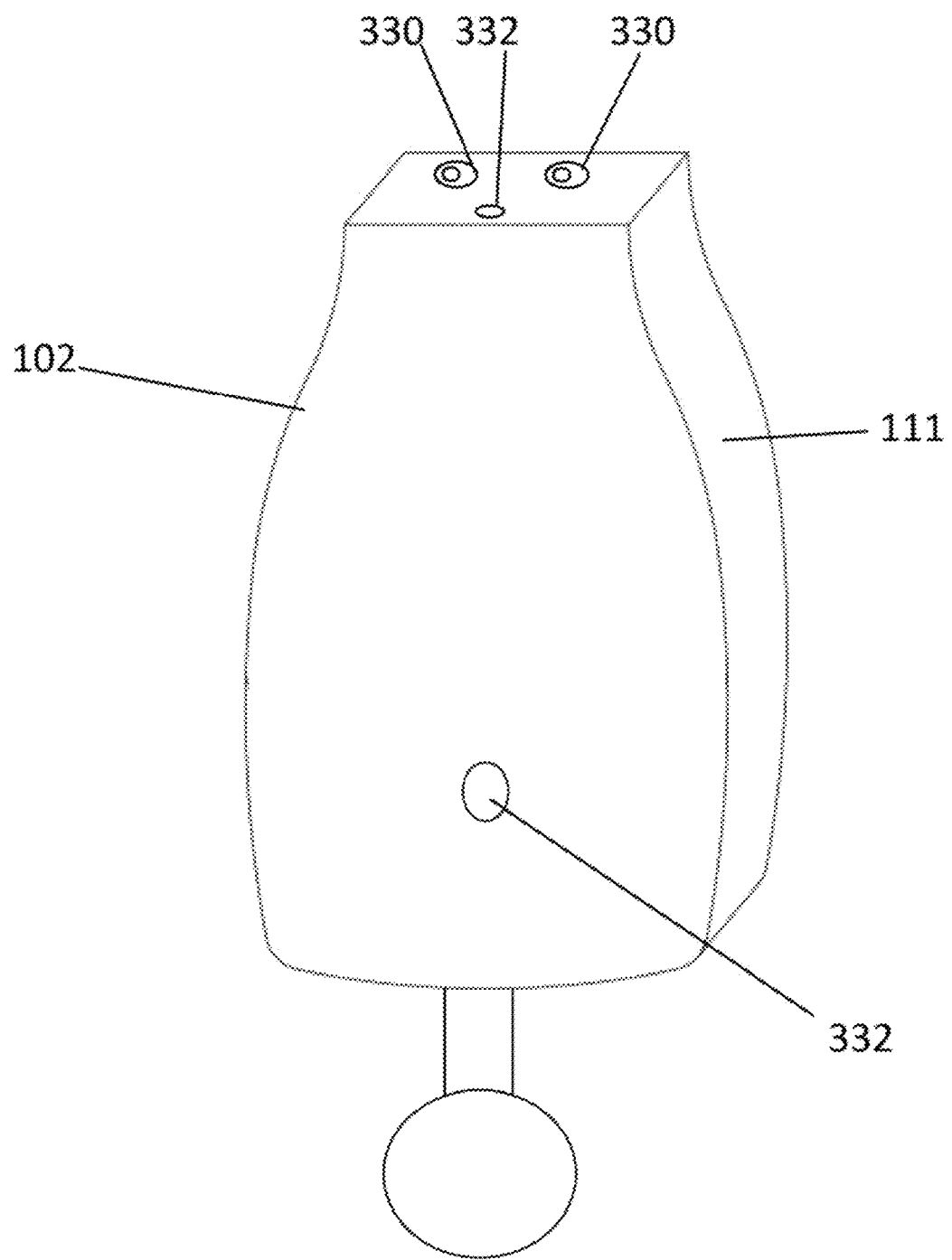
FIG. 3B is a rear-view illustration of the proximal portion of the delivery system handle according to embodiments of the present invention.

For further understanding, FIG. 3B depicts a back-side of the proximal portion 111 of the handle 102. In this non-limiting example, the proximal portion depicts two holes 330 for the arm tubes and hook wires to pass through to the pivotal member described above. Also shown are guide wire openings 332 for passage of the guide wire tube through and out of the proximal portion 111.

Figure 5:
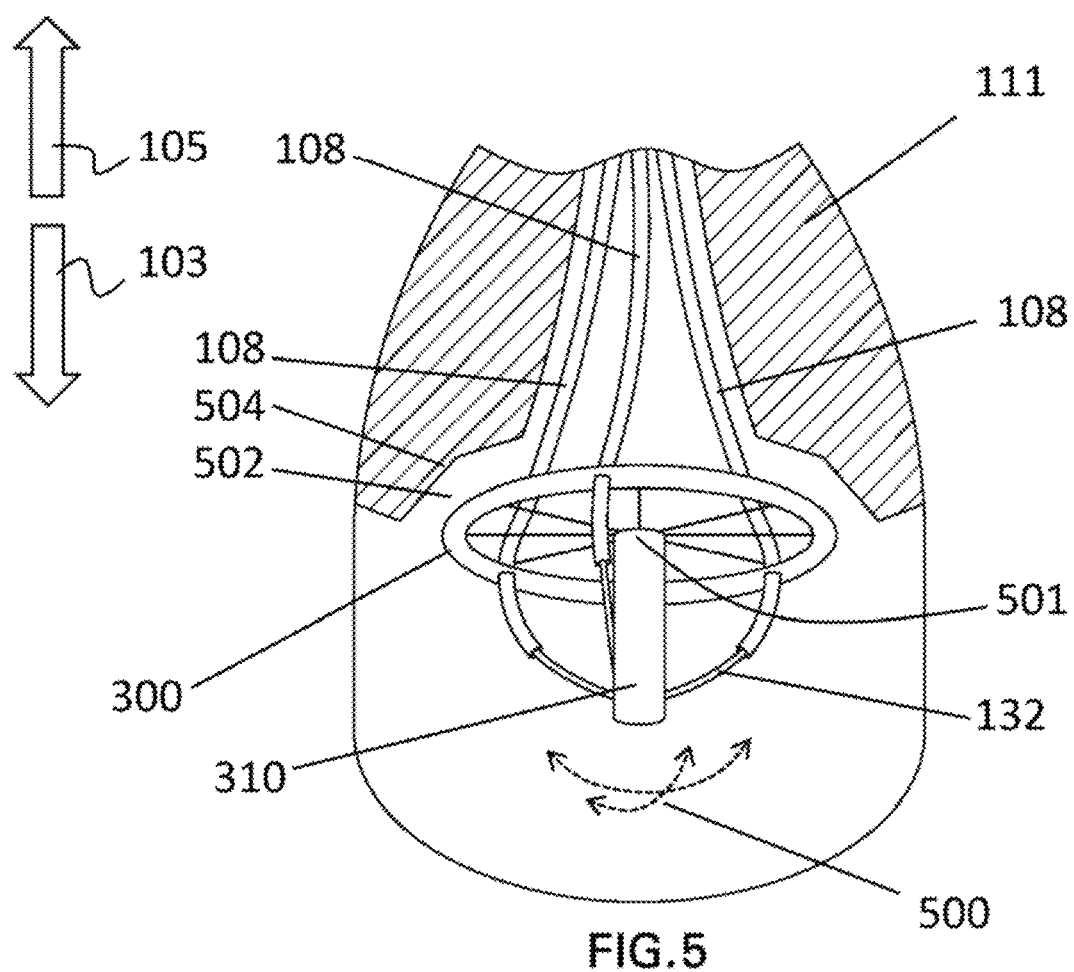
FIG. 5 is an illustration of the proximal portion of the delivery system handle according to embodiments of the present invention.

It should be noted that although two arms are depicted, the present invention is not intended to be limited thereto. For example, for a three or more arm delivery system (e.g., as may be preferred for a tricuspid valve), the arms may be connected to a structure (e.g., pivotal member) which may be pivoted about a point, and which when pivoted may advance or retract the attached arms in direction and in proportion to where the arms are connected to the structure, thereby causing the valve to tilt in the same direction(s) as the handle mechanism and in proportion to movement of the handle mechanism. For example, in one embodiment the pivotal member mechanism is ring-shaped (as shown in FIG. 5) or spherical-shaped. Stops can also be included in the handle to limit the range of motion for this tilting action. This aspect is described in further detail below regarding FIG. 5.

As noted above and as shown in the cut-away view of FIG. 4, the delivery system may be formed to include a way to flush the various components, including the sheath 104, splay shaft 106, arm tubes 130 and guide wire tube 140. For example, a fluid path 400 is designed into the sheath mount 200 with the sheath lumen 112 in the fluid path 400 at one end and with a seal 402 around the splay shaft 106 at the other end. Thus, fluid or other items introduced into the sheath flush port 222 via the flush valve 404 are allowed to pass through the fluid path 400 and the sheath lumen 112 to flush the sheath 104. Also noted in the figure is an adhesive 406 or other mechanism or technique for sealing and affixing the sheath 104 with the sheath mount 200.

Similarly, a fluid path 408 is designed into the splay shaft mount 202. The arm lumens 118 and guide-wire lumen 120 are in the fluid path at one end, with seals 410 around the arm tubes 130 and guide wire tube 140 at the other end. Holes 412 are shown in the sides of the arm tubes 130 and guide wire tube 140 within the fluid path 408 region. Thus, in this example, fluid or other items introduced into the splay shaft port 224 via the flush valve 414 are allowed to pass through the fluid path 408, through the lumen 118 and 120, and into the holes 412 to flush the splay shaft 106, arm tubes 130 and guide wire tube 140. Also noted in the figure is an adhesive 416 or other mechanism or technique for sealing and affixing the splay shaft 106 with the splay shaft mount 202.

As noted above, the delivery system can be formed, in various embodiments, to control a number of arms. FIG. 5, for example, depicts a proximal portion 111 of the delivery system handle with three arms 108 connected to a structure (i.e., pivotal member 300) which may be pivoted 500 about a pivot point 501. Thus, when pivoted, the pivotal member 300 advances 105 or retracts 103 the attached arms 108 in direction and in proportion to where the arms 108 are connected to the structure, thereby causing the valve to tilt in the same direction(s) as the handle mechanism and in proportion to movement of the handle mechanism. Unlike the aspect as shown in FIG. 3, the pivotal member 300 as shown in FIG. 5 is ring-shaped and can be referred to as a pivot ring. The proximal portion 111 of the handle can be formed such that the pivot ring or pivotal member 300 resides within a cavity 502 or space that is shaped to have limit stops 504 to limit the motion of the pivot ring and attached arms 108. Also shown is the valve release member 310 with the hook wires 132 extending therefrom.

Figure 1D:
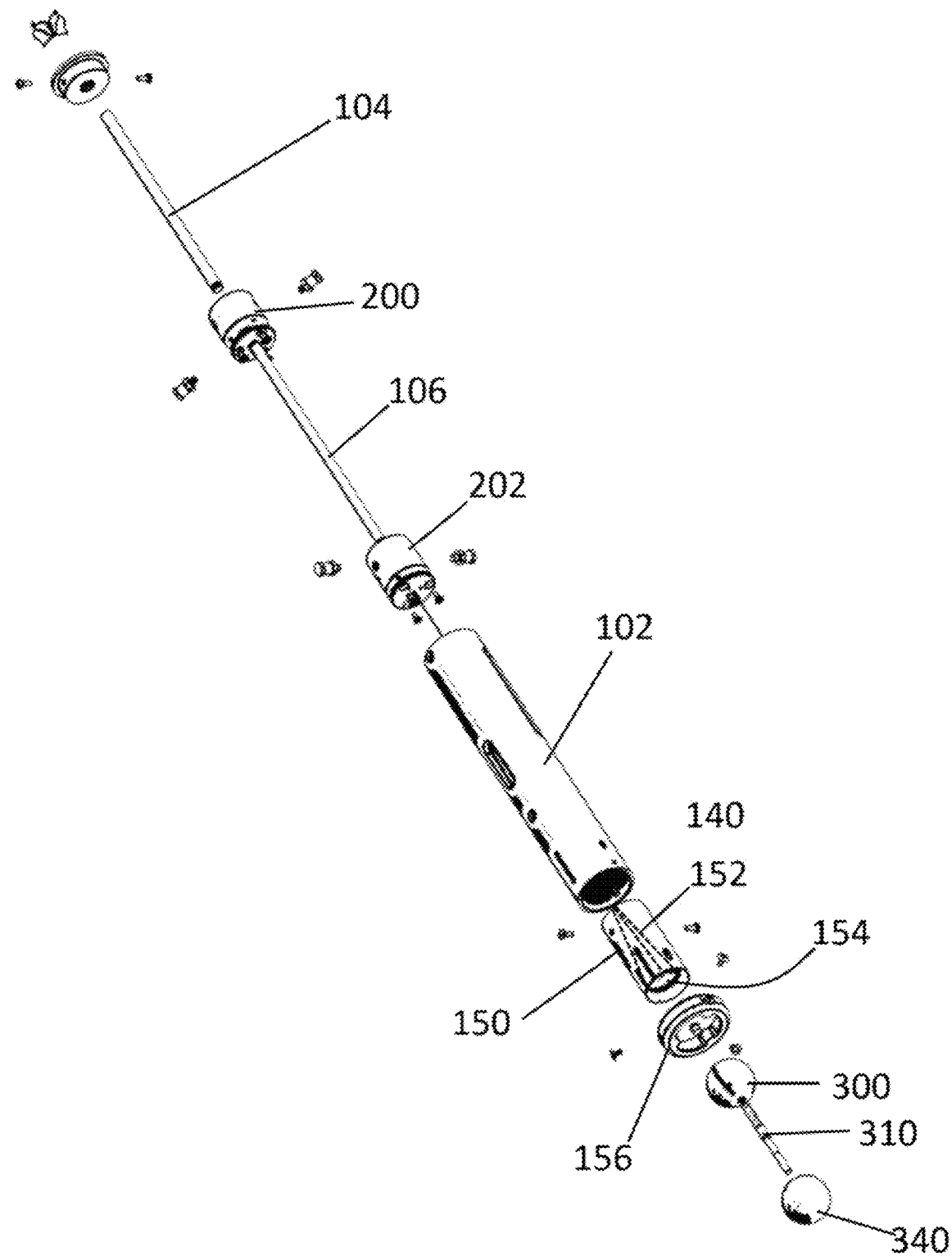
FIG. 1D is an exploded-view illustration of the handle as shown in FIG. 1C.

In other aspects, the pivotal member can be spherically-shaped (i.e., as a pivot sphere), or any other shape that allows for controlling of the two or more arms 108 based upon movement of the pivotal member 300. For example, the pivotal member can be spherically shaped (with the arms passing around a periphery of the sphere) and positioned within a ball joint or other encapsulate configuration that allows for rotation of the pivotal member in three-dimensions to selectively lengthen/shorten the arms in direction and proportion to where the arms are attached to the pivot mechanism. The non-limiting example as shown in FIG. 1C depicts the pivotal member 300 as a sphere or ball shape. The valve release member 310 is shown extending from the pivotal member 300 and handle 102. In this example, a handle ball 340 is attached with a proximal end of the valve release member 310. Thus, a user can use the handle ball 340 to laterally pivot 350 the attached pivotal member 300, which in turn advances or retracts the arms. The user could then press in the handle ball 340, which in turn depresses the valve release member 310 to cause the valve release member 310 to advance the hook wires and release the valve. For further understanding, FIG. 1D is an exploded-view illustration of the handle 102 configuration and embodiment as shown in FIG. 1C. As shown, the handle 102 includes the sheath mount 200 and splay shaft mount 202. The sheath 104 attaches with the sheath mount 104, while the splay shaft 106 attaches with the splay shaft mount 202 and passes through the sheath mount 200 and into the sheath 104. In this non-limiting example, an arm tube guide 150 is included and encased within the handle 102. The arm tube guide 150 includes arm channels 152 (e.g., lumen or pathways) formed therethrough to direct the arms toward a periphery of a socket 154 or receiving member that is formed to receive the pivotal member 300. Thus, when the arms are included, the arms are directed by the arm tube guide 150 toward a periphery of the pivotal member 300 (which in this example is a sphere or ball shape). The pivotal member 300 can then be locked into the socket 154 formed in a distal end of the arm tube guide 150 using an end cap 156 (e.g., ring shaped cap) or other suitable item. The valve release member 310 and corresponding handle ball 34 are also shown.

Figure 6:
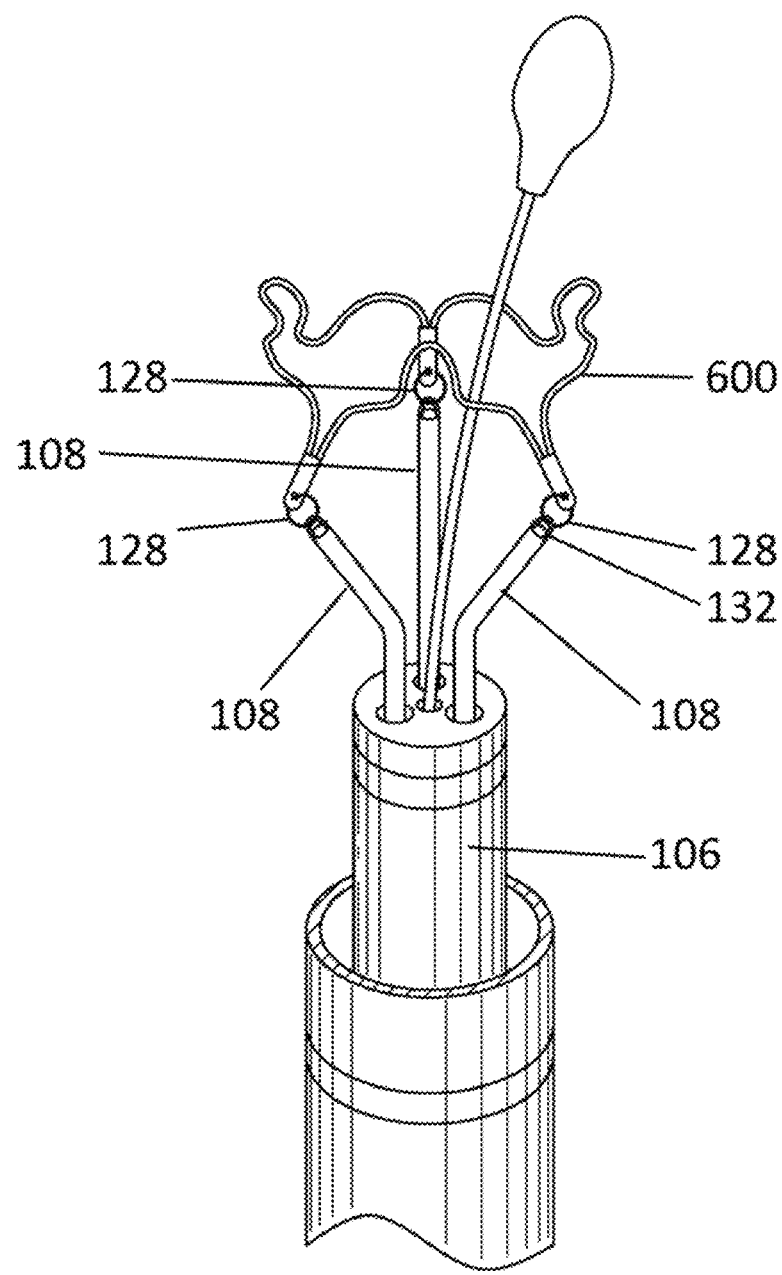
FIG. 6 is an illustration of a tri-leaflet valve frame as attached to a delivery catheter of the delivery system according to embodiments of the present invention.

Although not limited thereto, the aspect (ring or wheel configuration) as shown in FIG. 5 depicts three arms 108 extending from the pivotal member 300 which are desirably used for positioning and deploying a valve, such as a tri-leaflet valve (as shown in FIG. 6).

FIG. 6 illustrates a tri-leaflet valve frame 600 attached to the distal end of the delivery system. In this aspect, three arms 108 extend from the splay shaft 106. The hook wire 132 from each of the arms 108 is attached with the DSA 128 (i.e., loop) of the valve frame 600. Thus, in this aspect, the delivery system operates similarly to the configuration as shown in FIG. 1B, except that there are three arms 108 and the valve frame 600 is of a tri-leaflet valve as opposed to a bicuspid valve. In this example, the valve is connected to three or more arms 108 and the valve tilt is controlled by the position (distal vs proximal) of the arms 108. Importantly, the hook wires 132 are used throughout the aspects to allow a user to selectively release the valve upon implantation.

Figure 7:
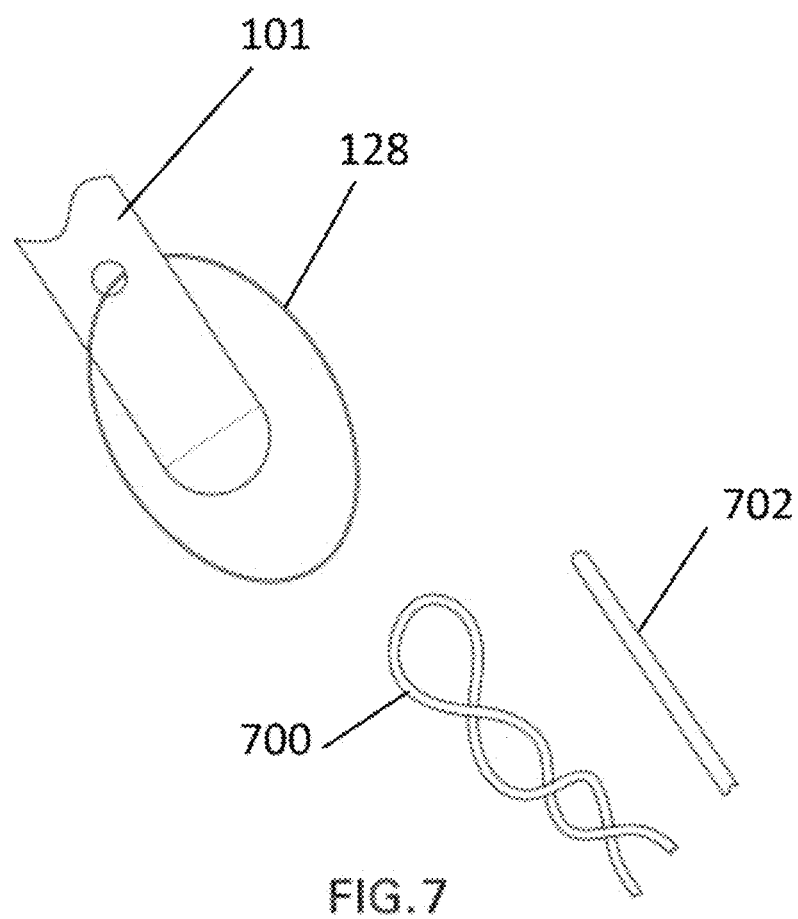
FIG. 7 is a close-up view illustration of a first attachment and release mechanism (referred to as trap and release) of the delivery system according, to embodiments of the present invention, depicting a valve frame with loop, a catheter arm, and a pin, showing the catheter arm in a twisted configuration.

As can be appreciated by those skilled in the art, there are a number of arm configurations by which the valve can be delivered and released from the delivery system. For example, FIGS. 7 through 12E illustrate a variety of trap and release mechanisms. Specifically, FIG. 7 illustrates a partial view of a valve frame 101 with a DSA 128 (i.e., loop), an arm 700, and a pin 702. In this configuration the arm 700 and pin 702 replace the hook wire as shown in previous examples and are referred to as a pin and twist wire construct. The arm 700 and pin 702 (in this and other configurations) are constructed of any suitable material, non-limiting examples of which include SS, Nitinol, or a suture.

Thus, the arm 700 and pin 702 reside within an arm tube with at least the pin 702 traversing back to the handle. The twisted arm 700 can pass into the arm rube partially or fully back to the handle and can be anchored at any suitable location (e.g., anchored to the pivotal member) such that the pin 702 can be moved relative to the arm 700. It is not necessary that it passes fully to the handle, whereas the pin 7002 passes back to the handle and valve release member to allow a user to operate the pin with the valve release member (e.g., such as pulling on the valve release member to retract the pin 702). The arm 700 in this example is shown in a twisted configuration. In this construct the pin 702 is moved proximally, relative to the arm 700, until it pulls out of the DSA 128, at which point the valve 101 is released from the delivery system. In this illustration the DSA 128 is attached to the valve 101 and release-ably attached to the delivery system.

Figure 8:
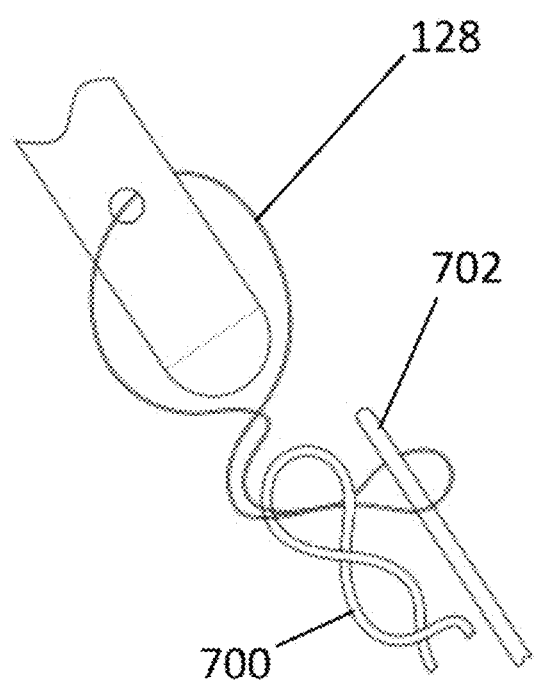
FIG. 8 is a close-up view illustration of the first attachment and release mechanism, depicting the loop as trapped.

FIG. 8 illustrates a partial-view similar to FIG. 7, except that the DSA 128 or loop is trapped. The figure depicts the DSA 128 as being passed through the arm 700 twist and the pin 702 is passed through DSA 128, thereby trapping the DSA 128 and securing the valve frame 101 to the arm 700.

Figure 9:
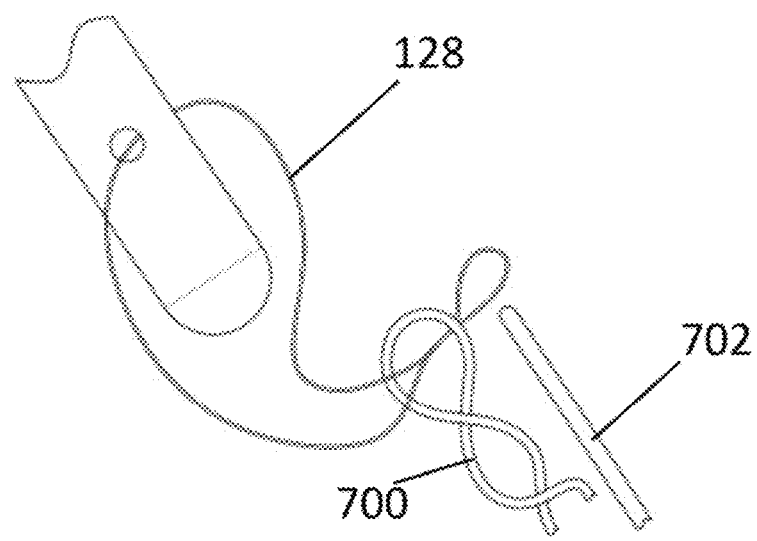
FIG. 9 is a close-up view illustration of the first attachment and release mechanism, depicted the loop as being released from the pin.

FIG. 9 illustrates a partial-view similar to that of FIG. 8, except that the DSA 128 or loop has been released from the pin 702. The pin 702 is moved (proximal in this illustration) out of the DSA 128 and the DSA 128 is no longer trapped and is released to slide out of arm 700 twist, disengaging the arm 700 from the valve 101.

Figure 10:
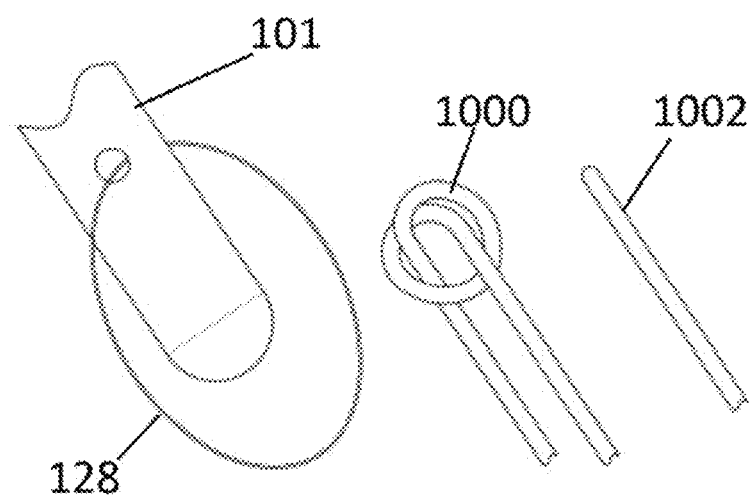
FIG. 10 is a close-up view illustration of the first attachment and release mechanism, depicting an alternate catheter arm configuration in which the catheter arm is in a hoop configuration.

FIG. 10 illustrates an alternate arm configuration, showing a partial view of the valve frame 101 with the DSA 128 (e.g., loop), and an arm 1000 and pin 1002 configuration referred to as the hoop configuration. As was the case above, the arm 1000 and pin 1002 in this configuration would replace the hook wire of previous embodiments as described above, with both the arm 1000 and pin 1002 residing with the aforementioned arm tube. Also as was the case above and as is the case in other aspects where an arm and pin replace the hook wire, the arm 1000 can pass into the arm tube partially or fully back to the handle and can be anchored at any suitable location (e.g., anchored to the pivotal member) such that the pin 1002 can be moved relative to the arm 1000. It is not necessary that it passes fully to the handle, whereas the pin 1002 passes back to the handle and valve release member to allow a user to operate the pin 1002 with the valve release member (e.g., such as pulling on the valve release member to retract the pin 1002).

Figure 11:
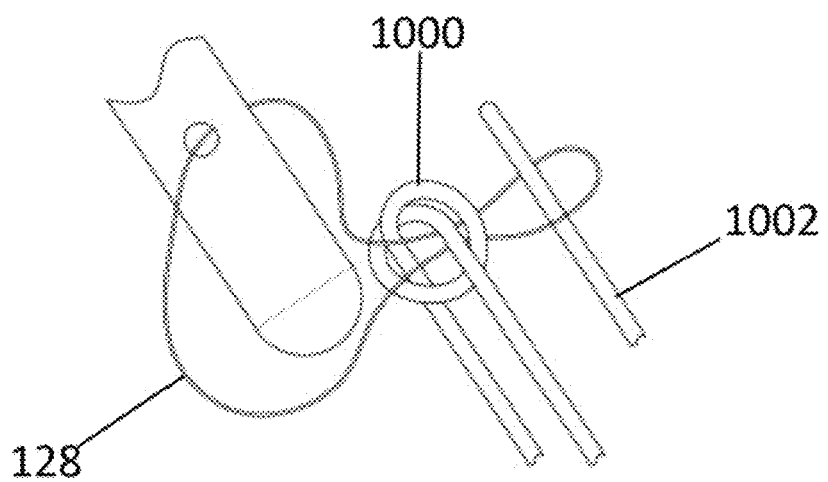
FIG. 11 is a close-up view illustration of the first attachment and release mechanism, depicting the loop as being trapped on the pin.

FIG. 11 is a partial view similar to FIG. 10, except that the DSA 128 or loop is trapped. As shown, the DSA 128 is passed through the arm 1000 hoop and the pin 1002 is passed through the DSA 128, thereby trapping the DSA 128 and securing the valve frame 101 to the arm 1000.

Figure 12A:
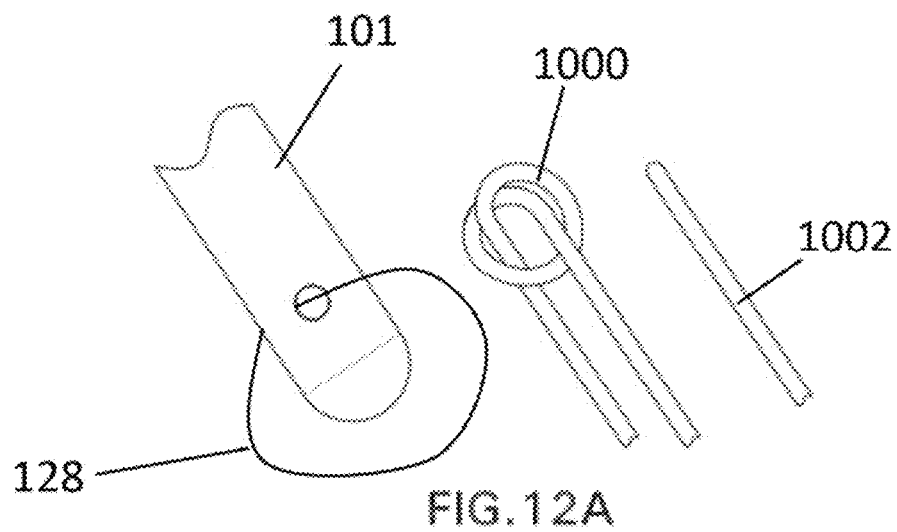
FIG. 12A is a close-up view illustration of the first attachment and release mechanism, depicting the loop as being released from the pin.

FIG. 12A is an illustration similar to that of FIG. 11, except that the DSA 128 is no longer trapped. The figure shows that the pin 1002 is moved (proximal in this illustration relative to an arm tube) out of the DSA 128 and the DSA 128 is no longer trapped and is released to slide out of the arm 1000 hoop, disengaging the arm 1000 from the valve.

Figure 12B:
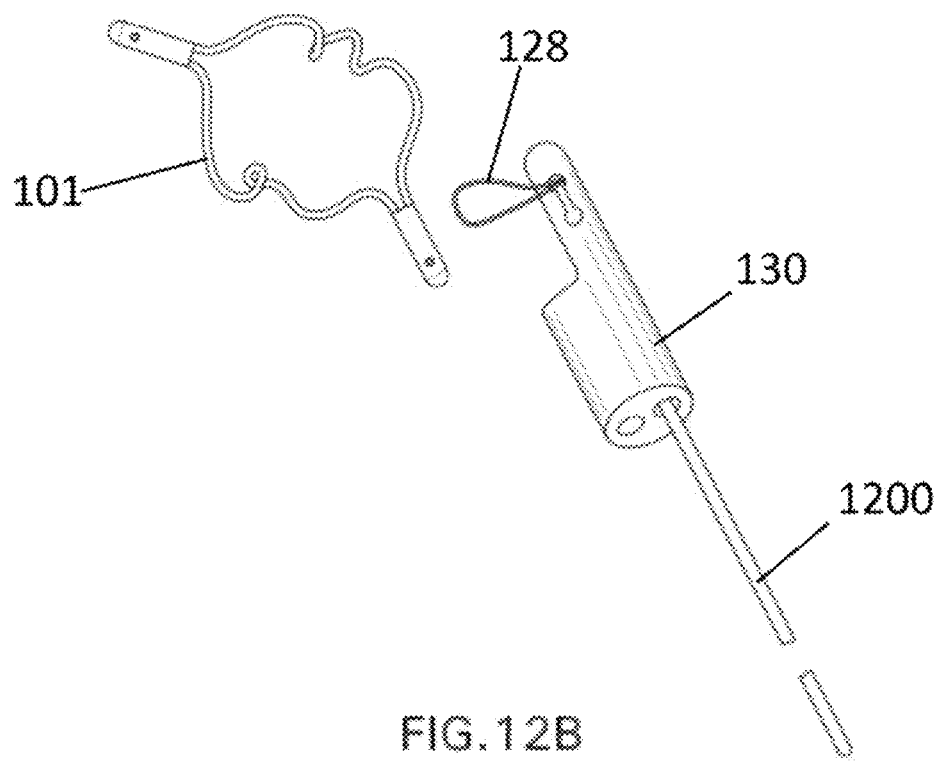
FIG. 12B is a close-up view illustration of the first attachment and release mechanism, depicting an alternative configuration in which the loop is attached to the catheter arm time rather than to the valve frame (as depicted in FIGS. 1, and 6 through 12A)

FIG. 12B is an illustration of yet another configuration of trap and release, showing a pin 1200 within the arm tube 130. The partial view of FIG. 12B illustrates the DSA 128 (e.g., loop) as anchored or attached to the arm tube 130 rather than to the valve frame 101. Also shown is the pin 1200 that passes from the handle and through the arm tube 130 until reaching the distal portion of the arm tube 130 as shown in FIG. 12B.

Figure 12C:
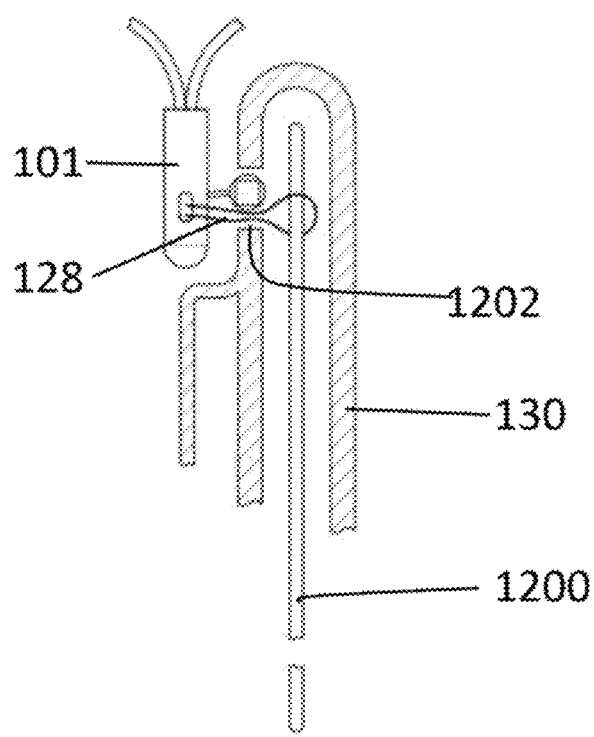
FIG. 12C is sectional-view illustration of the attachment and release mechanism as depicted in FIG. 12B.

FIG. 12C is an illustration of a section view of FIG. 12B. In this aspect, the DSA 128 or loop is anchored to the arm tube 130 and is positioned through the frame 101 and back through a hole 1202 in the arm tube 130. The pin is positioned through the DSA 128 or loop to secure the frame 101 to the delivery system. When the pin 1200 is pulled proximal, it slides out of the DSA 128, thereby releasing the valve 101 from the delivery system as the DSA 128 slides out of the frame 101.

Figure 12D:
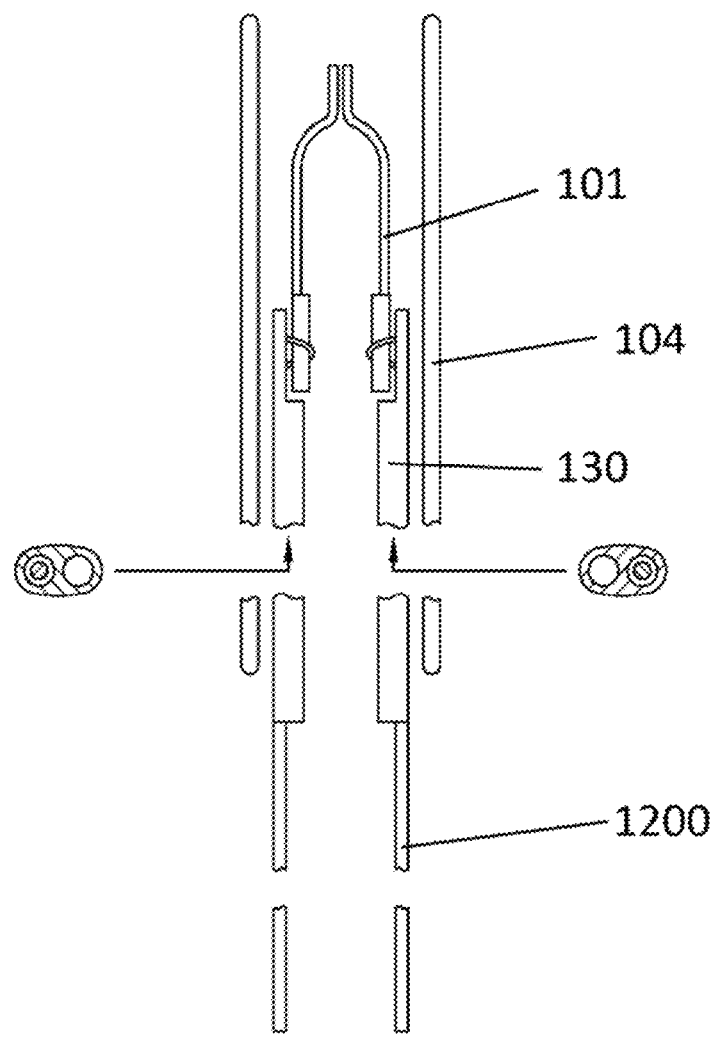
FIG. 12D is a sectional-view illustration of a valve inside the sheath, depicting the valve as connected to the delivery system with the alternative pin and tube configuration (as shown in FIGS. 12B and 12C)

FIG. 12D is a sectional-view of a valve 101 inside the sheath 104, with the valve 101 connected to delivery system with the alternative pin 1200 and arm tube 130 configuration as shown in FIGS. 12B and 12C.

Figure 12E:
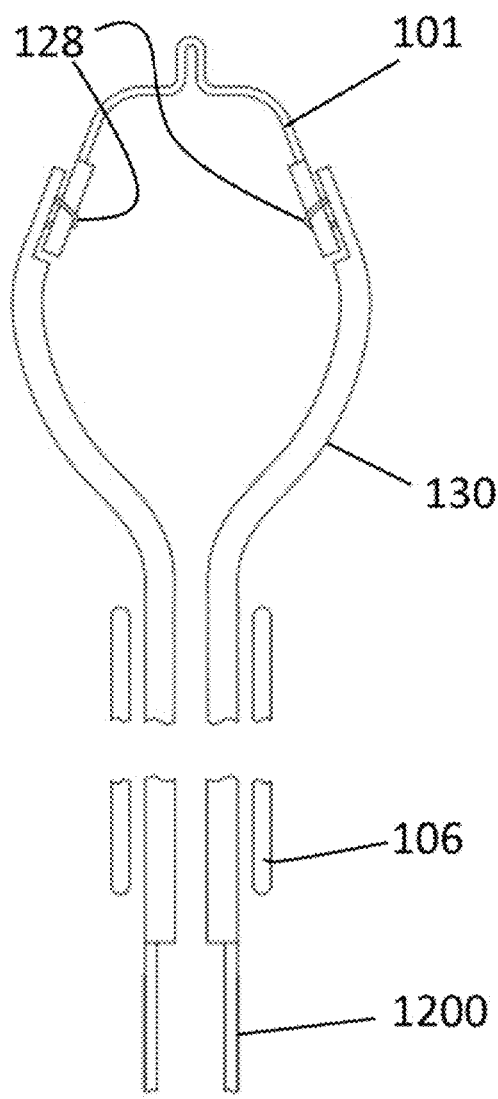
FIG. 12E is a sectional-view illustration of the valve deployed outside of the sheath, depicting the valve as connected to the delivery system with the alternative pin and tube configuration (as shown in FIGS. 12B, 12C, and 12D)

For further understanding, FIG. 12E is a sectional-view showing the valve 101 as deployed outside of sheath and splay shaft 106, with the valve 101 connected to delivery system with the alternative pin 1200 and arm tube 130 configuration (as shown in FIGS. 12B, 12C, and 12D). Thus, in the pin and arm tube construct shown in FIGS. 12B through 12E, the pin 1200 is moved proximally, relative to the arm tube 130, until it pulls out of the DSA 128 and the valve 101 is released from the delivery system and deployed.

Another configuration of the attachment and release mechanism is depicted in FIGS. 13 through 16, which is referred to as the hook and release construct. Although not intended to be limited thereto, it should be noted that the hook and release construct is also illustrated for exemplary purposes in FIGS. 1A through 6. In this construct and as shown in FIGS. 13 through 16, the DSA 128 is release-ably connected to a hook wire 132 trapped in an arm tube 130. When the arm tube(s) 132 is/are moved proximally and/or the hook wire(s) 132 is/are moved distally, relative to the arm tube(s) 130 a sufficient distance (e.g., between one and fifteen millimeters, or any other pre-configured distance), the hook wire 132 exits the arm tube 130. Upon exiting the arm tube 130, the hook wire(s) 132 substantially self-straightens, thereby releasing the DSA 128 and valve 101 from the delivery system. In this construct the DSA 101 is attached to the valve 101 and release-ably attached to the delivery system. The hook wire 132 self-straighten, for example, because they are formed of a shape-memory material, such as Nitinol or any other suitable material.

Figure 13:
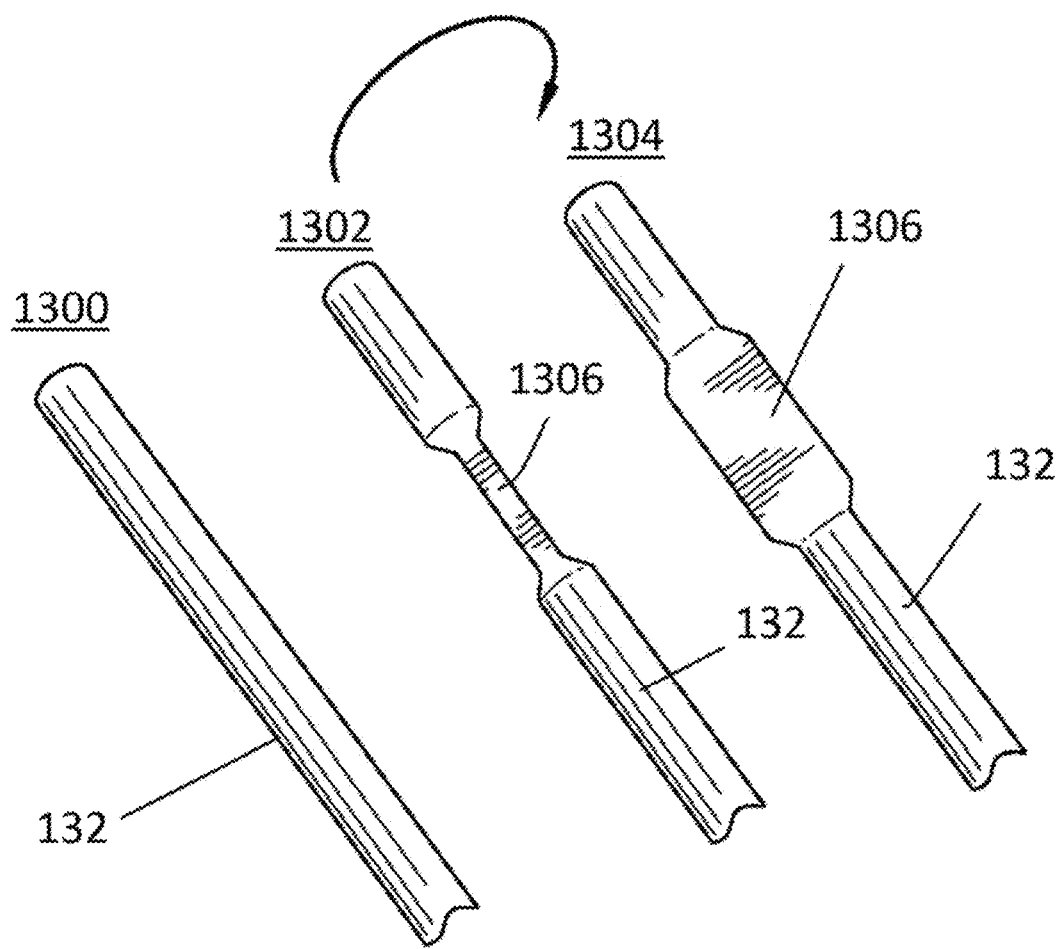
FIG. 13 is a partial-view illustration of a second attachment and release mechanism (referred to as hook and release), showing a distal end of a hook wire before and after swage in zero and ninety degree perspectives.

For further understanding, FIG. 13 is a partial-view illustration, showing the distal end of hook wire 132 (as would be positioned through the arm tube shown throughout the figures (e.g., FIGS. 1A through 6). FIG. 13 depicts the hook wire 132 before swage 1300 and after swage in 0 degree 1302 and 90 degree 1304 perspectives, all in straight condition. The hook wire 132 can be swaged such that it is more flexible in a direction transverse to the plane of the thin swage cross-section than relative to a direction transverse to the plane of the thick cross-section and also relative to unswagged section(s). Thus, the hook wire 132 is swaged to allow the swaged section 1306 to be bent to a desirable angle and radii (i.e., forming a hook) when positioned within the arm tube and substantially self-straighten from this angle and radii when released from the arm tube.

Figure 14A:
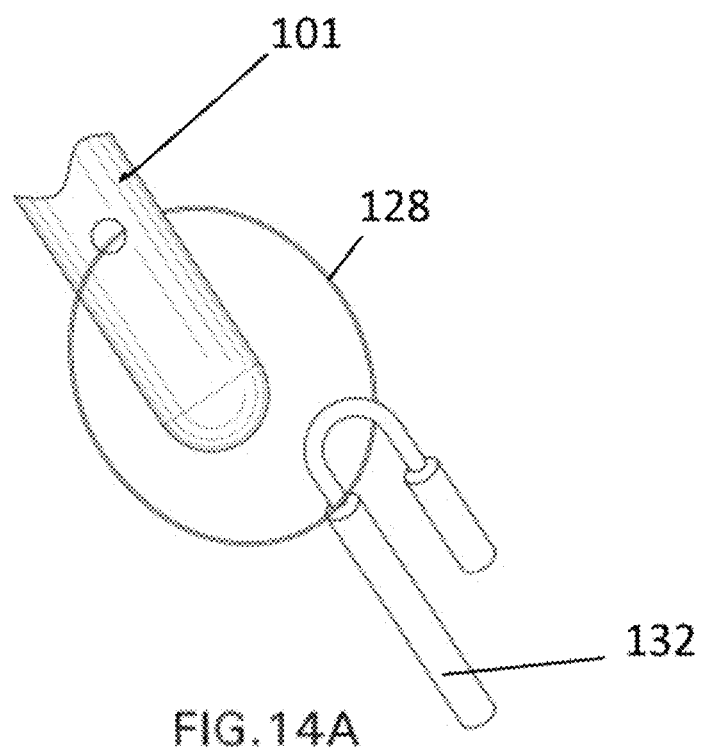
FIG. 14A is a partial-view illustration of the second attachment and release mechanism, showing the valve frame and loop with the loop around the distal end of the hook wire to hook the loop.

For example, FIG. 14A is an illustration showing the valve frame 101 and DSA 128 (e.g., loop) with the DSA 128 hooked around the distal end of the hook wire 132. Thus, the hook wire 132 is shown curved to hook the loop or DSA 128.

Figure 14B:
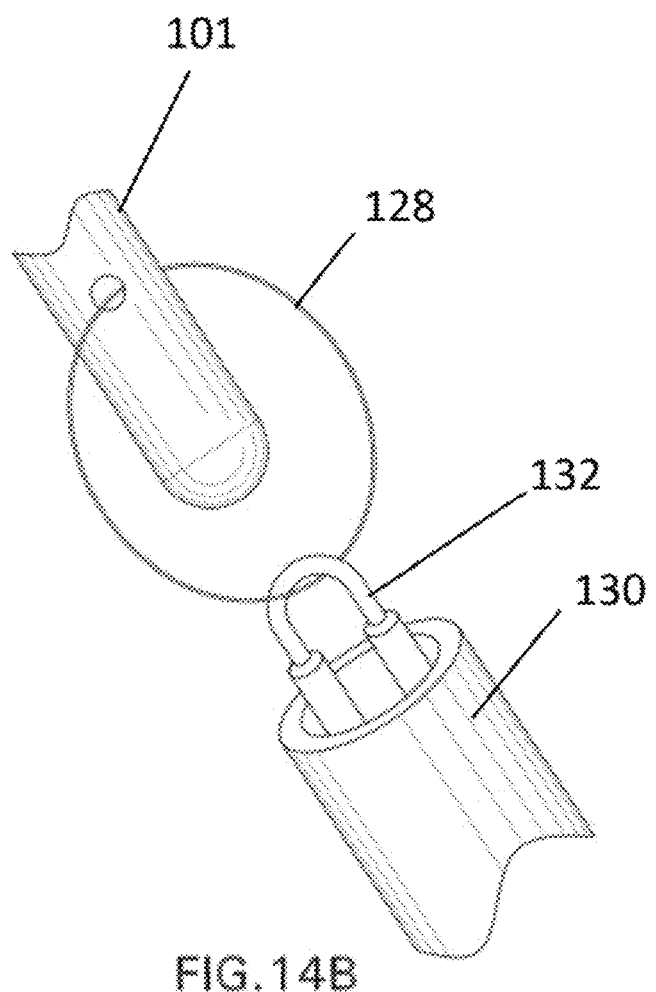
FIG. 14B is a partial-view illustration of the second attachment and release mechanism, showing an arm tube partially positioned around the hook wire.

FIG. 14B is an illustration showing the arm tube 130 partially positioned around the hook wire 132. The hook wire 132 may be withdrawn into arm tube(s) 130 and/or the arm tube(s) 130 may be advanced over the hook wire 132.

Figure 14C:
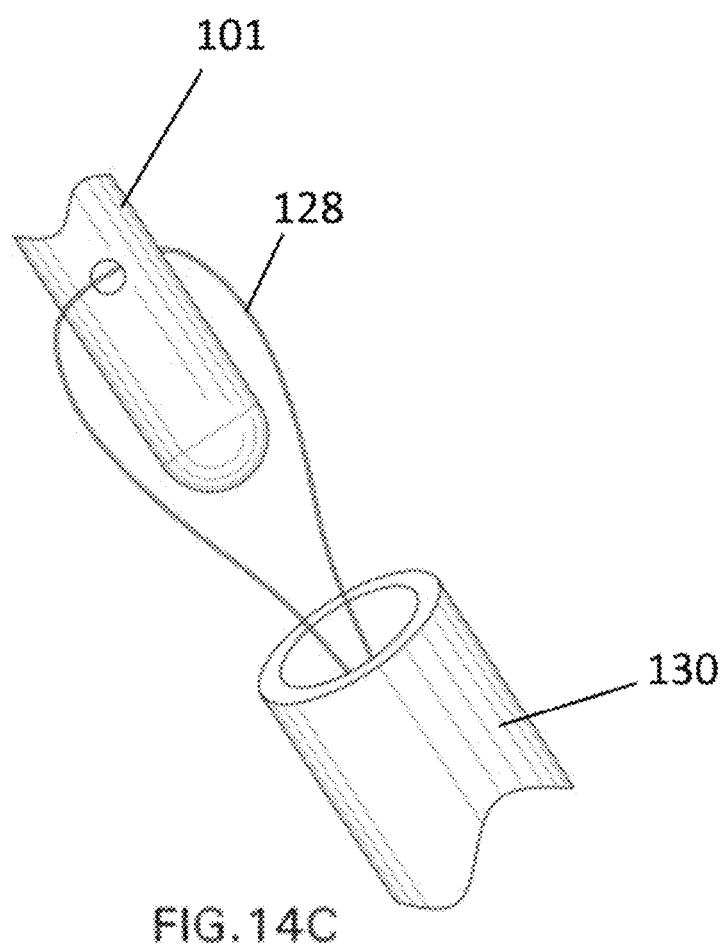
FIG. 14C is a partial-view illustration of the second attachment and release mechanism, showing the arm tube(s) fully positioned around the hook wire(s)
Figure 14D:
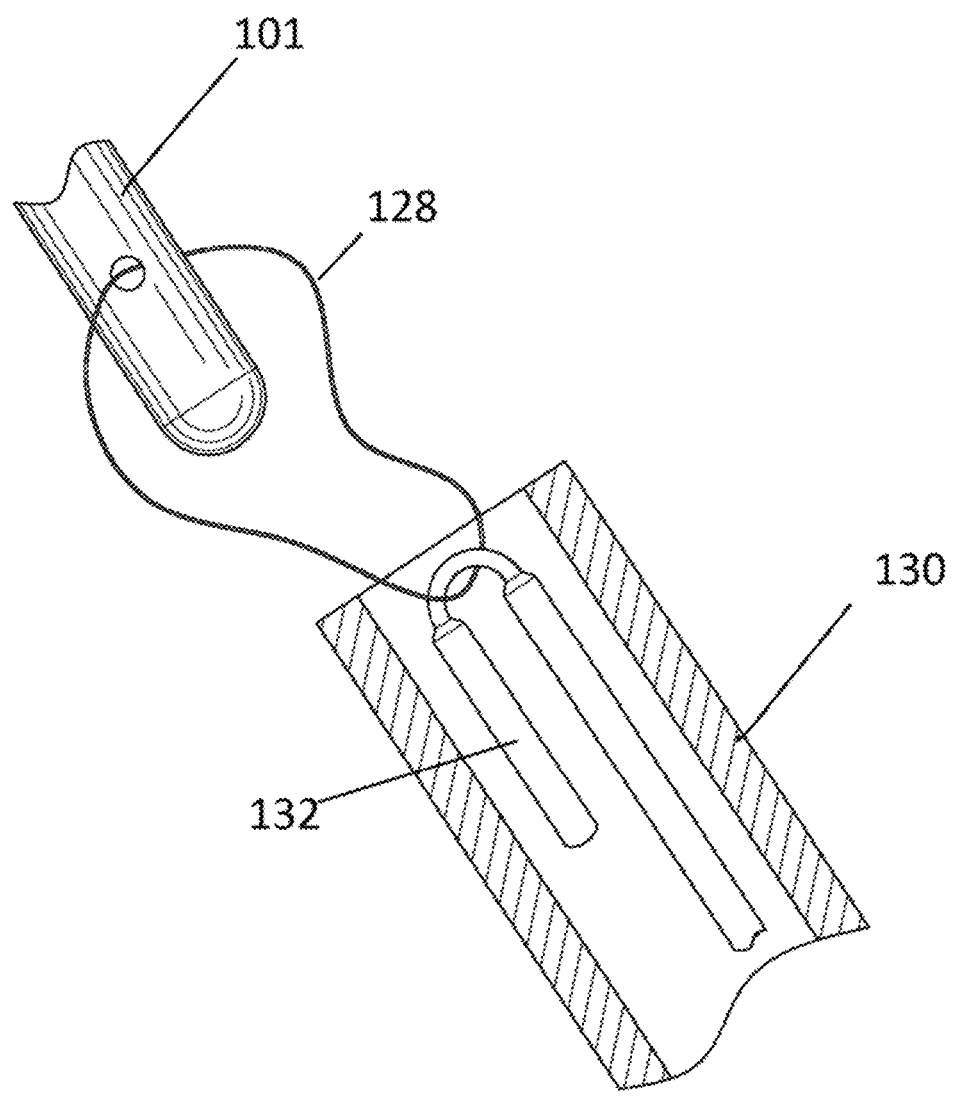
FIG. 14D is a partial, cross-sectional view illustration of the second attachment and release mechanism, depicting the loop hooked to the hook wire, with the hook wire constrained in an approximately 180° bend by the arm tube.

FIG. 14C is an illustration showing the arm tube(s) 130 fully positioned around the hook wire(s) (which is enclosed within the arm tube 130). In a desired embodiment, the inner diameter of the arm tube 130 is smaller than the length of the unswagged distal end-section of the hook wire. Further, the unswagged distal end-section of the hook wire is sufficiently rigid such that it would not bend under working tensile loads to be applied via the DSA 128 to the hook wire. Thus, the hook wire is prevented from straightening while the arm tube(s) 130 is(are) positioned around the hook wire. In the configuration shown in FIG. 14C, the valve 101 is securely attached to the delivery system. For further understanding, FIG. 14D is a cross-sectional view of the arm tube 130, showing the DSA 128 (e.g., loop) hooked to the hook wire 132, with the hook wire 132 constrained in an approximately 180° bend by the arm tube 130.

Figure 15:
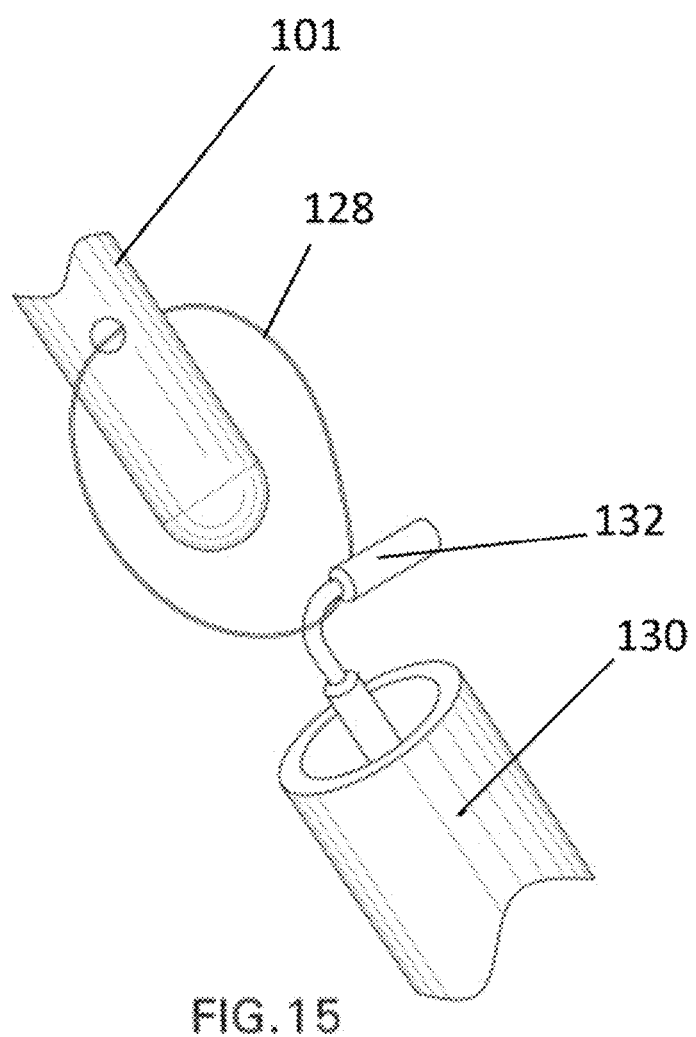
FIG. 15 is a partial-view illustration of the second attachment and release mechanism, showing an arm tube being moved proximal relative to the hook wire (and/or vice versa) and the hook wire substantially self-straightening after it is no longer constrained by the arm tube.

FIG. 15 is an illustration depicting the arm tube 130 being moved proximal relative to the hook wire 132 (and/or vice versa) and the hook wire 132 substantially self-straightening after it is no longer constrained by the arm tube 130. For example, movement of the valve release member (described above) causes the hook wires 132 to advance through the arm tubes 130 which in turn causes a distal end of the hook wires 132 to extend from a distal end of the arm tubes 130.

Figure 16:
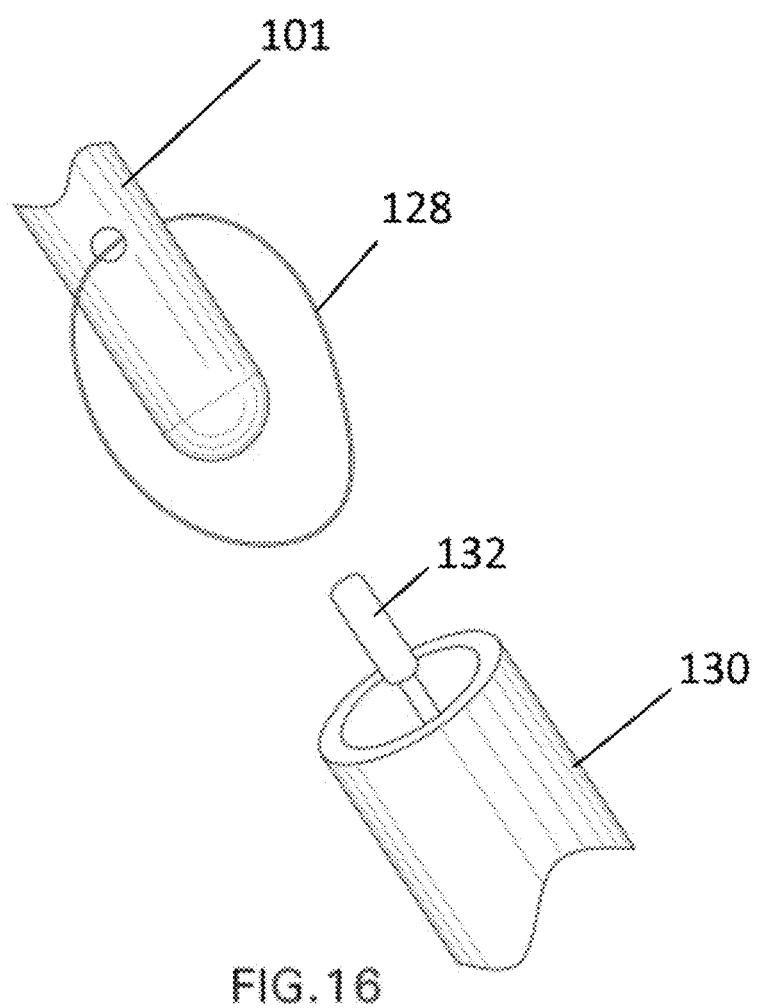
FIG. 16 is a partial-view illustration of the second attachment and release mechanism, showing the loop fully released from the arm and the hook wire being positioned back into the arm tube.

FIG. 16 is an illustration depicting the DSA 128 (e.g., loop) fully released from the arm and the hook wire 132 being withdrawn back into the arm tube 130 and/or the arm tube 130 being extended over the hook wire 132. Thus, the valve 101 is released from the delivery system.

Figure 17:
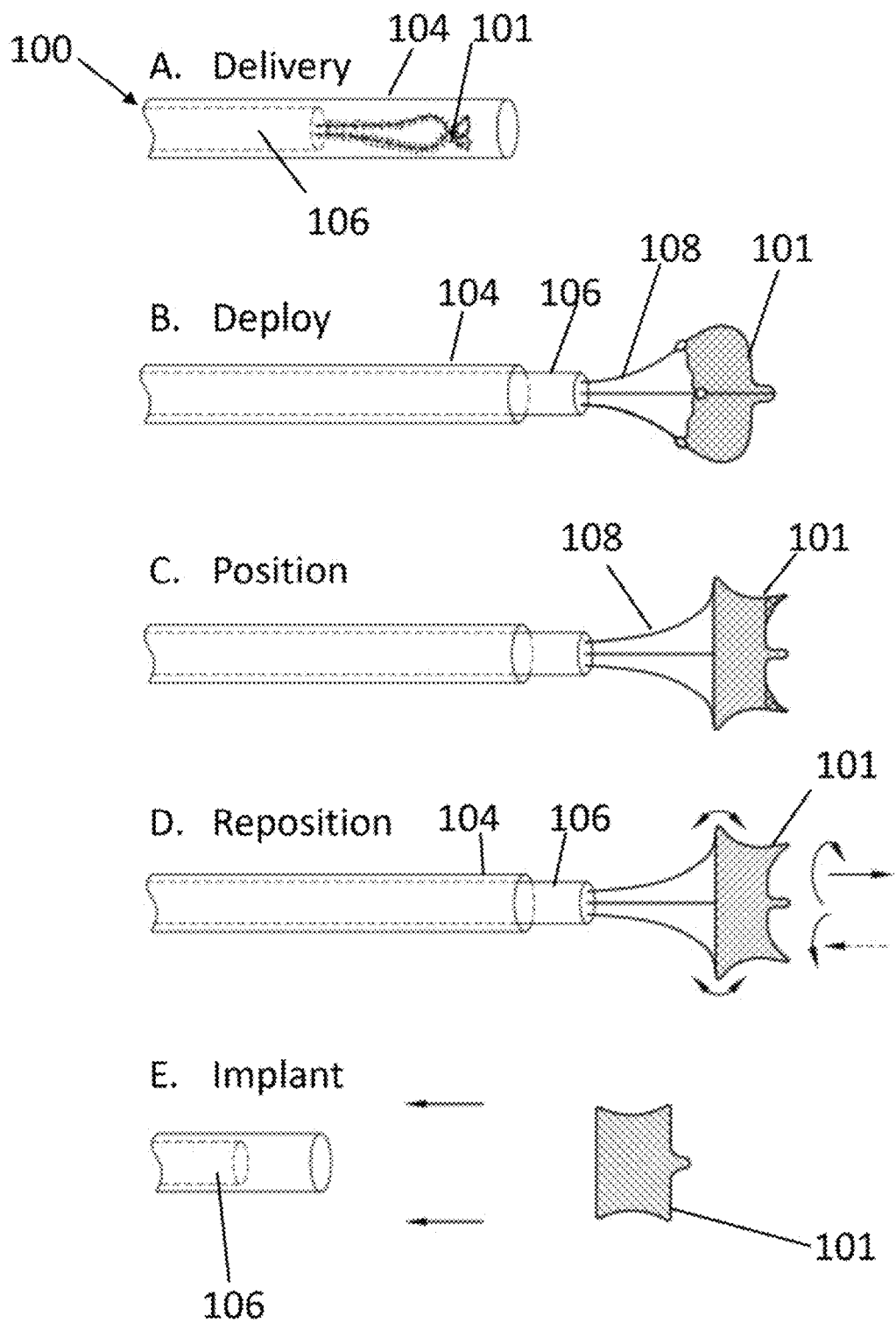
FIG. 17 is an illustration depicting steps of using a delivery system according to embodiments of the present invention to deliver and implant a valve through a transapical approach.
Figure 18:
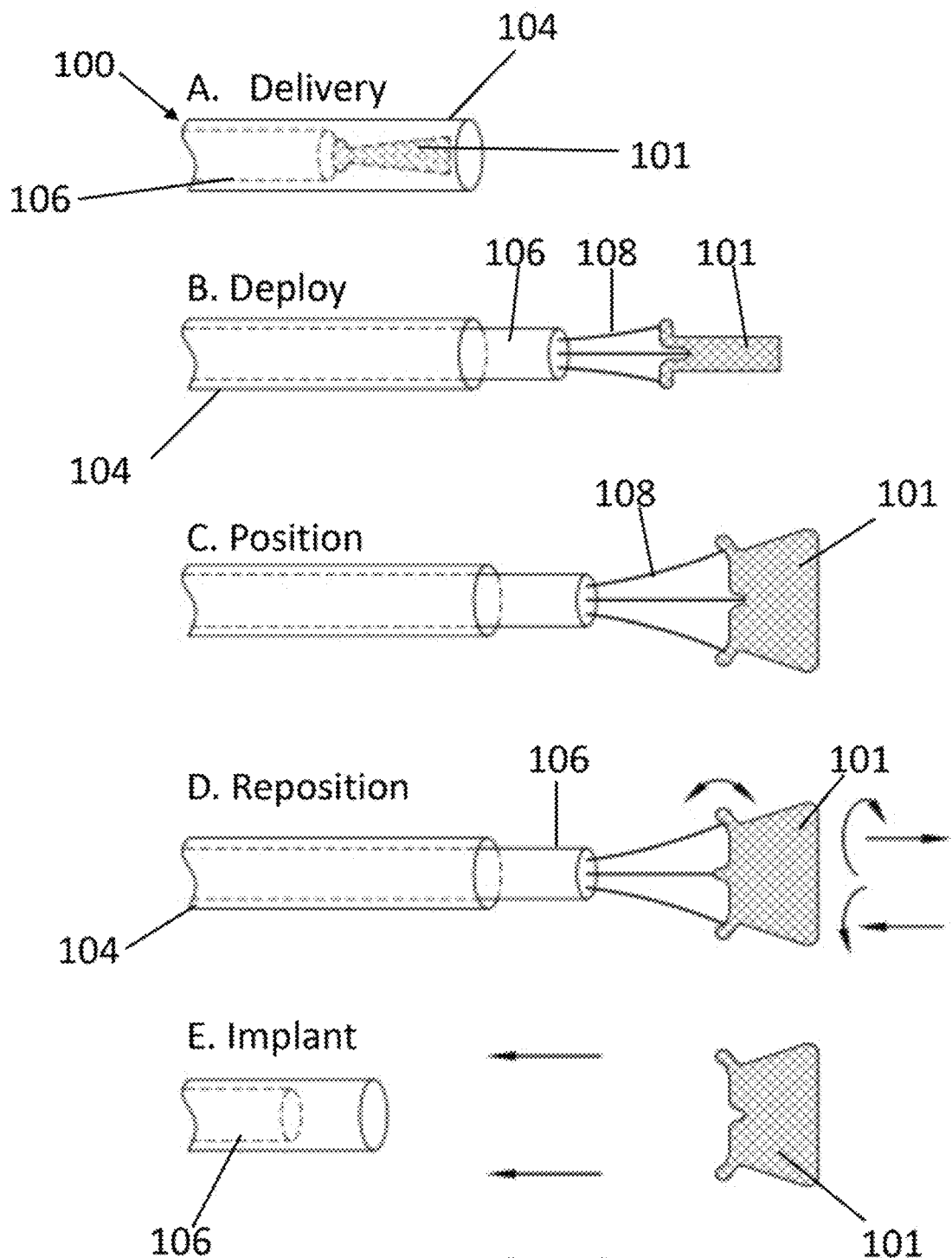
FIG. 18 is an illustration depicting steps of using a delivery system according to embodiments of the present invention to deliver and implant a valve through a anterograde approach.

As understood by those skilled in the art, the delivery system described herein can be used to delivery and implant a variety of heart valves and other implants through a variety of approaches. As a non-limiting example, FIG. 17 depicts a transapical approach for delivery, while FIG. 18 depicts delivery through an anterograde approach. The general procedure for delivery and implantation of atrioventricular heart valves is as follows (note that this procedure can be performed for both the transapical approach (of FIG. 17) and anterograde approach (of FIG. 18)).

Figure 19:
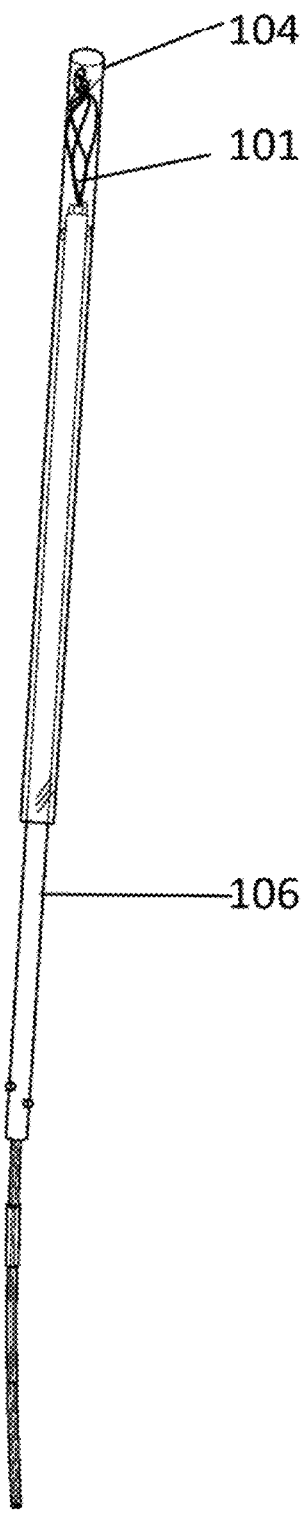
FIG. 19 is an illustration of the sheath with the heart valve encased therein.
Figure 20:
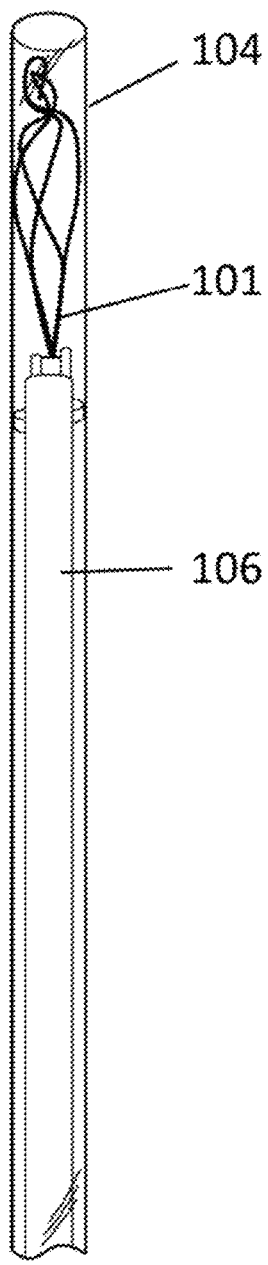
FIG. 20 is a close-up illustration depicting the heart valve as encased within the sheath for delivery.

Delivery includes transcatheter delivery of the valve 101 to inside the heart chamber. During delivery and as shown in FIGS. 19 and 20, the splay shaft 106 is positioned with the sheath 104 and the valve 101 is protectably encased within the sheath 104. The delivery system 100 is positioned and rotated to align with respect to the native valve's anterior/posterior leaflets.

Deployment includes deploying the heart valve 101 from the delivery system. When at the desired position, the sheath 104 is retracted (partially or fully). The distal side of the valve 101 frame expands in the native valve's annulus. The splay shaft 106 is at least partially retracted to allow the arm(s) to be retracted without pulling the connected valve frame against the distal end of the splay shaft.

Positioning includes tilting the valve 101 and aligning it perpendicular to the native annulus by extending at least one arm 108 while retracting the other(s), as needed. This can be done, for example, by manipulating the pivotal member as described above (which is a mechanism designed into the handle such that at least two arms 108 move in opposite or different directions). During positioning, the user lightly pulls the valve 101 frame proximal to catch the frame's atrial-catches on atrial side of the native annulus.

If necessary, the valve 101 can be repositioned. For example, the pivotal member can be used to tilt the valve 101 in an opposite direction, advance the splay shaft 106, advance the sheath 104, and/or axially rotate the valve 101.

Once in the desired position, the valve 101 can be implanted and released. This process includes, for example, fully retracting the splay shaft 106, implanting the valve 101, and verifying that it is properly implanted (e.g., through radioscopy, etc.). The valve 101 then expands to its fully formed shape when the splay shaft is fully retracted. Thereafter, the delivery system is withdrawn from the patient.

It should also be noted that in some circumstances it may be desirable to resheath/recapture the valve 101 multiple times to find the best moment/location to release. For example, if the valve needs to get repositioned to an entirely different location or any other repositioning as desired, the splay shaft 106 and sheath 104 can be selectively advanced to position the valve 101 back into the sheath. Also, this mechanism allows full valve recapture 101 (prior to complete release), if the procedure encounter any problem and allow a user to withdraw the valve 101 as may be needed.

Thus, in summary, this disclosure provides a delivery system 100 for percutaneous delivery of heart valves 101 and a method for attaching and releasing such valves 101. The delivery system 100 includes arms 108 that can be pre-shaped or otherwise formed to splay apart when released. A splay shaft 106 is used to straighten the arms 108 when the splay shaft 106 is advanced forward over the arms 108 (or the arms 108 are drawn into the splay shaft 106) which also compresses the proximal end of the valve 101. The arms 108 are allowed to recover their shape when the splay shaft 106 is pulled back (or the arms are advanced forward) to expose the arms 108, which also allows the proximal end of the valve 101 to self-expand. The various components described herein provide a method of being able to tilt the valve 101 in a plane, by selectively lengthening/shortening the arms 108 using the handle 102 and its various components (e.g., pivotal member) for activating the arms 108 in opposite direction and equal amount. For example, the valve 101 can be tilted in three-dimensions by selectively lengthening/shortening the arms 108 in direction and proportion to where the arms 108 are attached to the pivot mechanism (e.g., pivotal member). Once in the desired location, the arms 108 can be released from the valve 101 to implant the valve 101.

Finally, while this invention has been described in terms of several embodiments, one of ordinary skill in the art will readily recognize that the invention may have other applications in other environments. It should be noted that many embodiments and implementations are possible, and that the various components described herein can be interchanged or used in any combination as desired. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A delivery system for percutaneous delivery and implantation of a heart valve, comprising:
a handle;

at least two arms extending from the handle, the at least two arms operable for holding and implanting a heart valve;

a sheath extending from the handle, the sheath having a sheath lumen;

a splay shaft extending from the handle through the sheath lumen;

wherein the at least two arms extend from the handle through the splay shaft;

a sheath controller housed within the handle and affixed with the sheath, the sheath controller operable for allowing a user to selectively advance or retract the sheath to constrain or expose a heart valve when attached with the at least two arms; and a splay shaft controller housed within the handle and affixed with the splay shaft, the splay shaft controller operable for allowing the user to selectively advance or retract the splay shaft to constrain or expose the at least two arms, the splay shaft controller having:

a splay shaft mount movably attached with the handle, wherein the splay shaft mount is fixedly connected with a proximal end of the splay shaft such that the splay shaft projects from the splay shaft mount and through a sheath mount into a sheath; and a splay shaft motion control attached with the splay shaft mount, whereby a user can utilize the splay shaft motion control to move the splay shaft mount within the handle and thereby selectively advance or retract the splay shaft.

2. The delivery system as set forth in claim 1, further comprising a guide wire tube extending from the handle through the splay shaft, the guide wire tube providing a guide wire lumen for passage of a guide wire.

3. The delivery system as set forth in claim 2, wherein each arm comprises an arm tube with a hook wire passing therethrough.

4. The delivery system as set forth in claim 3, wherein the sheath controller comprises:

a sheath mount movably attached with the handle, wherein the sheath mount is fixedly connected with a proximal end of the sheath;

a sheath motion control attached with the sheath mount, whereby a user can utilize the sheath motion control to move the sheath mount within the handle and thereby selectively advance or retract the sheath.

5. The delivery system as set forth in claim 4, further comprising an arm controller attached with handle and the at least two arms, the arm controller operable for allowing a user to selectively advance or retract at least a portion of the at least two arms.

6. The delivery system as set forth in claim 5, wherein the arm controller is a pivotal member and the at least two arms attached are attached with the pivotal member such that pivotal motion of the pivotal member about an axis causes at least one arm to advance while retracting at least one other arm.

7. The delivery system as set forth in claim 6, wherein the at least two arms extend around the pivotal member and through the splay shaft mount and into the splay shaft.

8. The delivery system as set forth in claim 7, further comprising a valve release attached with the handle for allowing a user to selectively release a heart valve as attached with the at least two arms.

9. The delivery system as set forth in claim 8, wherein the valve release is a valve release member movably attached with the pivotal member, wherein the valve release member is fixedly attached with the hook wires, with the arm tubes being fixedly attached with the pivotal member, such that movement of the valve release member causes the hook wires to advance through the arm tubes which in turn causes a distal end of the hook wires to extend from a distal end of the arm tubes.

10. The delivery system as set forth in claim 9, wherein a distal end of the hook wire is swaged to allow the hook wire to easily bend into a hook shape to constrain a loop thereon.

11. The delivery system as set forth in claim 10, wherein the at least two arms are formed such that when constrained within the splay shaft, they are relatively straight, and when the splay shaft is retracted such that a distal portion of the at least two arms extend from the splay shaft, the at least two arms splay apart from one another.

12. The delivery system as set forth in claim 11, further comprising a third arm, such that the at least two arms in conjunction with the third arm comprises three arms, with the three arms being attached with the pivotal member such that tilting the pivotal member cause each of the three arms to selectively lengthen or shorten in direction and proportion to where each of the three arms are attached to the pivotal member.

13. The delivery system as set forth in claim 12, wherein the pivotal member is spherically shaped with the three arms passing around a periphery of the pivotal member.

14. The delivery system as set forth in claim 13, further comprising a safety catch, the safety catch operable for selectively inhibiting motion of the valve release member, thereby preventing inadvertent release of a heart valve.

15. The delivery system as set forth in claim 1, further comprising an arm controller attached with handle and the at least two arms, the arm controller operable for allowing a user to selectively advance or retract at least a portion of the at least two arms.

16. The delivery system as set forth in claim 15, wherein the arm controller is a pivotal member and the at least two arms attached are attached with the pivotal member such that pivotal motion of the pivotal member about an axis causes at least one arm to advance while retracting at least one other arm.

* * * * *